(12) United States Patent
Oraevsky et al.

(10) Patent No.: US 11,160,456 B2
(45) Date of Patent: Nov. 2, 2021

(54) LASER OPTOACOUSTIC ULTRASONIC IMAGING SYSTEM (LOUIS) AND METHODS OF USE

(71) Applicants: Alexander A. Oraevsky, Houston, TX (US); Sergey A. Ermilov, Houston, TX (US); Andre Conjusteau, Houston, TX (US); Mark Anastasio, St. Louis, MO (US)

(72) Inventors: Alexander A. Oraevsky, Houston, TX (US); Sergey A. Ermilov, Houston, TX (US); Andre Conjusteau, Houston, TX (US); Mark Anastasio, St. Louis, MO (US)

(73) Assignee: Tomowave Laboratories, Inc., Houston, TX (US)

( * ) Notice: Subject to any disclaimer, the term of this patent is extended or adjusted under 35 U.S.C. 154(b) by 11 days.

(21) Appl. No.: 13/748,498

(22) Filed: Jan. 23, 2013

(65) Prior Publication Data

US 2013/0190595 A1    Jul. 25, 2013

Related U.S. Application Data

(60) Provisional application No. 61/605,276, filed on Mar. 1, 2012, provisional application No. 61/632,387, filed on Jan. 23, 2012.

(51) Int. Cl.
*A61B 5/00* (2006.01)
*A61B 8/08* (2006.01)
*A61B 8/00* (2006.01)

(52) U.S. Cl.
CPC .......... *A61B 5/0095* (2013.01); *A61B 5/0035* (2013.01); *A61B 5/708* (2013.01);
(Continued)

(58) Field of Classification Search
CPC ....... A61B 5/708; A61B 8/483; A61B 5/0095; A61B 5/0097; A61B 2562/14;
(Continued)

(56) References Cited

U.S. PATENT DOCUMENTS 5,840,023 A * 11/1998 Oraevsky ............. A61B 5/0095
367/7
6,216,025 B1 * 4/2001 Kruger .......................... 600/407
(Continued)

FOREIGN PATENT DOCUMENTS

WO    WO 2010080991 A2 *  7/2010

OTHER PUBLICATIONS

Kruger et al. "Thermoacoustic Molecular Imaging of Small Animals". Molecular Imaging, vol. 2, No. 2, Apr. 2003, pp. 113-123.*
(Continued)

*Primary Examiner* — Amanda Lauritzen Moher
(74) *Attorney, Agent, or Firm* — Benjamin Aaron Adler

(57) ABSTRACT

Provided herein are the systems, methods, components for a three-dimensional tomography system. The system is a dual-modality imaging system that incorporates a laser ultrasonic system and a laser optoacoustic system. The dual-modality imaging system generates tomographic images of a volume of interest in a subject body based on speed of sound, ultrasound attenuation and/or ultrasound backscattering and for generating optoacoustic tomographic images of distribution of the optical absorption coefficient in the subject body based on absorbed optical energy density or various quantitative parameters derivable therefrom. Also provided is a method for increasing contrast, resolution and accuracy of quantitative information obtained within a subject utilizing the dual-modality imaging system. The method comprises producing an image of an outline boundary of a volume of interest and generating spatially or temporally (Continued)

coregistered images based on speed of sound and/or ultrasonic attenuation and on absorbed optical energy within the outlined volume.

4 Claims, 16 Drawing Sheets

(52) U.S. Cl.
CPC .......... *A61B 8/0825* (2013.01); *A61B 8/4416* (2013.01); *A61B 8/483* (2013.01); *A61B 5/4312* (2013.01); *A61B 2562/14* (2013.01); *A61B 2562/146* (2013.01); *A61B 2576/00* (2013.01)

(58) Field of Classification Search
CPC .......... A61B 2562/146; A61B 2576/00; A61B 5/0035; A61B 5/4312; G01N 21/1702; G01N 2021/1706; G01N 2021/1708
See application file for complete search history.

(56) References Cited

U.S. PATENT DOCUMENTS

| | | | |
|---|---|---|---|
| 6,635,486 B2 | 10/2003 | D'Souza et al. | |
| 8,686,335 B2* | 4/2014 | Schmid | G01N 21/1702 250/205 |
| 8,997,571 B2* | 4/2015 | Someda | A61B 5/0095 73/579 |
| 9,128,032 B2* | 9/2015 | Carson | A61B 5/0059 |
| 9,759,689 B2* | 9/2017 | Guo | H04B 10/27 |
| 2004/0067000 A1* | 4/2004 | Bates | A61B 5/0097 385/7 |
| 2006/0184042 A1* | 8/2006 | Wang | A61B 5/0073 600/476 |
| 2006/0272419 A1* | 12/2006 | Maris et al. | 73/606 |
| 2007/0238958 A1* | 10/2007 | Oraevsky | A61B 5/0073 600/407 |
| 2007/0287912 A1* | 12/2007 | Khuri-Yakub | A61B 5/0059 600/439 |
| 2008/0173093 A1* | 7/2008 | Wang et al. | 73/602 |
| 2010/0152591 A1 | 6/2010 | Yu et al. | |
| 2010/0249570 A1* | 9/2010 | Carson | A61B 5/0059 600/407 |
| 2011/0301458 A1* | 12/2011 | Li et al. | 600/437 |
| 2012/0065490 A1* | 3/2012 | Zharov | A61B 5/0059 600/407 |
| 2013/0168532 A1* | 7/2013 | Schmid | G01N 21/1702 250/205 |

OTHER PUBLICATIONS

Oraevsky et al. "Two-Dimensional Opto-Acoustic Tomography Transducer Array and Image Reconstruction Algorithm". Proc. SPIE 3601, Laser-Tissue Interaction X: Photochemical, Photothermal, and Photomechanical, 256 (Jun. 14, 1999); doi:10.1117/12.350007.*

Buma et al. "A high frequency ultrasound array element using thermoelastic expansion in PDMS." Proceedings of the IEEE Ultrasonics Symposium 2:1143-1146. Feb. 2001.*

Yaseen, et al., Optoacoustic imaging of the prostateL development toward image-guided biopsy. Journal of Biomedica Optics, 15(2), 021310, Mar./Apr. 2010.

Harrison et al., Combined photoacoustic and ultrasound biomicroscopy, Optics Express 22041, vol. 17, No. 24, 23, Nov. 23, 2009.

* cited by examiner

Gruneisen parameter $\Gamma = (A * s^2)/C$
  A - volumetric coef of expansion
  s - speed of sound
    C - heat capacity at P=const

| Material | s, m/s | A, 1/K | C, J/(g*K) | $\Gamma$ |
|---|---|---|---|---|
| Alcohol (ethanol) | 1144 | 0.00109 | 2.44 | 0.58464 |
| Ethylene glycol | 1644 | 0.00057 | 2.41 | 0.639236 |
| Glycerol (glycerine) | 1904 | 0.0005 | 2.38 | 0.7616 |
| Mercury | 1450 | 0.00018 | 0.1395 | 2.712903 |
| Olive oil | 1430 | 0.0007 | 2 | 0.715715 |
| Water, 20°C | 1482 | 0.000207 | 4.1818 | 0.108719 |
| Water, 37°C | 1523 | 0.0003605 | 4.1782 | 0.200132 |
| Gold | 3240 | 0.0000426 | 0.129 | 3.466649 |
| Silver | 3650 | 0.0000585 | 0.233 | 3.34492 |
| Copper, annealed | 4760 | 0.0000498 | 0.385 | 2.930775 |
| Aluminum | 6420 | 0.0000666 | 0.897 | 3.060214 |
| Platinum | 3260 | 0.000027 | 0.133 | 2.157483 |

FIG. 6

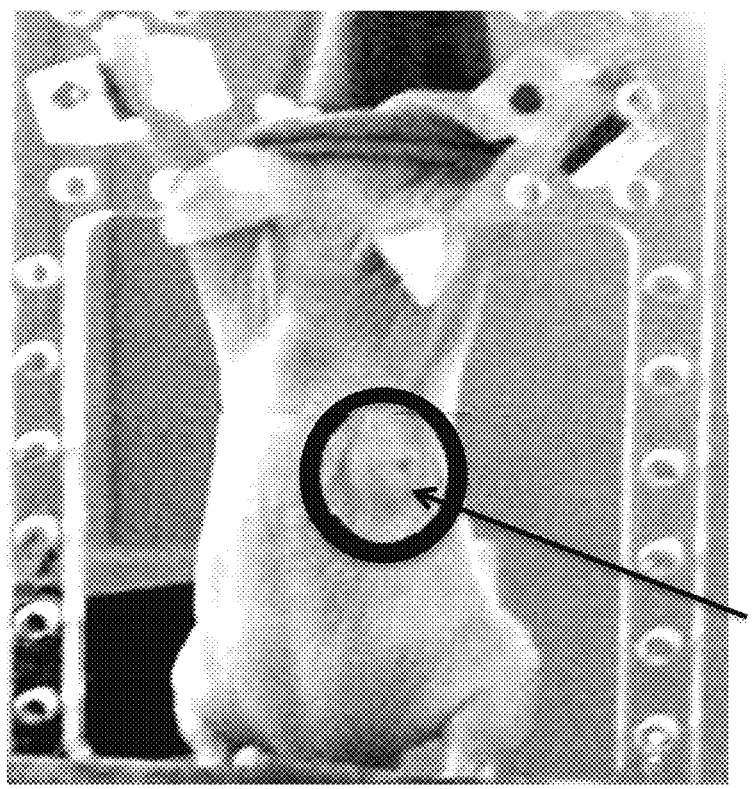
FIG. 16A
Tumor
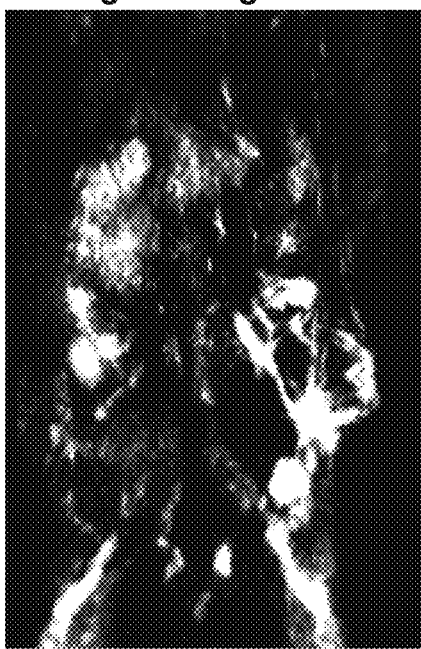
FIG. 16B  FIG. 16C

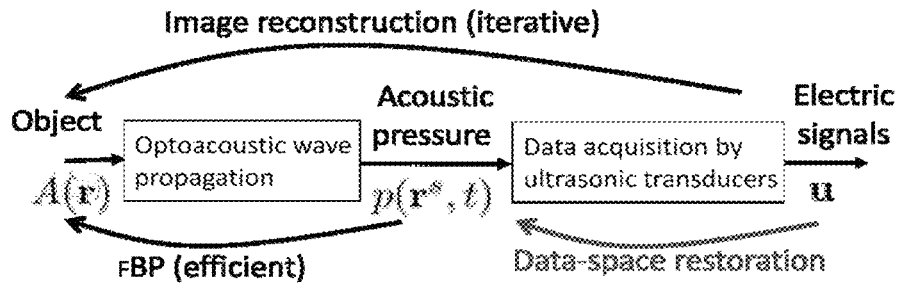

Smooth curves of optoacoustic pressure sinograms can be sparsely represented by curvelets:

$$p(\mathbf{r}^s, t) = \sum_\mu [\theta]_\mu \gamma_\mu(\mathbf{r}^s, t)$$

– $g_\mu$: curvelets
– q: curvelet coefficient vector
– Sparsity: most elements of q equal zero

• Sparsity can be employed as a *priori* information to regularize data restoration without loss of resolution and quantitative info $$\hat{\theta} = \arg\min_\theta \|\mathbf{u} - \mathbf{H}^s \mathbf{C}^T \theta\|^2 + \lambda \|\theta\|_1$$
$$\mathbf{p} = \mathbf{C}^T \hat{\theta}$$

FIG. 18

LASER OPTOACOUSTIC ULTRASONIC IMAGING SYSTEM (LOUIS) AND METHODS OF USE

CROSS-REFERENCE TO RELATED APPLICATIONS

This non-provisional application claims benefit of priority under 35 U.S.C. § 119(e) of provisional application U.S. Ser. No. 61/632,387, filed Mar. 1, 2012 and of provisional application U.S. Ser. No. 61/605,276, filed Jan. 23, 2012, now abandoned, both of which are hereby incorporated by reference.

BACKGROUND OF THE INVENTION

Field of the Invention

The present invention relates to the field of biomedical imaging and discloses the designs and methods used for a tomographic system that can provide comprehensive medical information about a portion of the body under examination. More specifically, the present invention provides a Laser Optoacoustic Ultrasonic Imaging System (LOUIS) for three-dimensional tomography of a subject or portion or body part thereof.

Description of the Related Art

Imaging internal structures of a human or animal subject body has been a subject of many inventions. There are systems that use ultrasound pressure waves, photon waves and acoustic waves induced by absorption of photons in tissues of the subject body. However, the prior art lacks a system that can provide comprehensive information about tissues, including anatomical structure (morphology) and molecular composition simultaneously with information about tissue normal or abnormal function. The most detailed and comprehensive information can be provided by high resolution three dimensional maps, especially valuable if such maps are provided in real time, i.e. faster than the time required for certain changes to occur in the subject body. Medically important changes may occur in the subject body on the time scale as long several minutes and as short as fraction of a second. Therefore, the most ideal system can provide detailed (high resolution) three-dimensional functional and anatomical maps (images) of the subject body or least certain organs of the subject body.

Laser ultrasound method and systems designed for non-destructive evaluation of materials such as metals, ceramics and fiber-epoxy composites have been discussed in the literature. However, these systems are not three-dimensional tomography systems and their design cannot be used for biomedical imaging. Methods and materials for laser generation of ultrasonic pulses have been discussed in the prior art (7) and proposals have been made by O'Donnell group for application of such pulses in 3D and 2D ultrasonic imaging in medicine. However, the prior art lacks description of a design for 3D laser ultrasound tomography system capable of volumetric visualization of biomedical objects through algorithms of reconstruction tomography, such as filtered back-projection tomography and of the full set of properties of the layers of the materials for the most effective generation of ultrawide-band ultrasound with laser pulses. Three-dimensional ultrasound tomography has been proposed for biomedical imaging, specifically for the volumetric imaging of breast cancer. However, the ultrasound pulses in these systems are generated through application of electrical voltage pulses to piezoelectric elements.

Optoacoustic tomography is used in biomedical applications for in vivo and in vitro imaging of animal and human tissues and organs based on differences in tissue optical properties. Optoacoustic tomography has the potential to become valuable modality of functional molecular imaging. The essence of functional molecular imaging is to provide quantitative information (maps) of distributions and concentrations of various molecules of interest for medicine. For example, distribution of hemoglobin and oxi-hemoglobin concentration in tissue shows whether the tissue normally functions or it is damaged or malignant. Distribution of specific protein receptors in cell membranes give insight into molecular biology or cells helping in designing drugs and therapeutic methods to treating human diseases.

Laser optoacoustic imaging systems and methods have been disclosed by Oraevsky et al (8,9), Kruger et al. (10-11) and others (12-18). However, the prior art lacks description of a 3D tomography system that combines laser ultrasonic and laser optoacoustic tomography in one imaging module, allows natural coregistration of volumetric images acquired and reconstructed using the two modalities and thereby provides the most comprehensive anatomical, functional and molecular information for the physician or biomedical researcher.

The prior art contains some limited information about the idea of combining the laser optoacoustic imaging and the laser ultrasonic imaging. Specifically, the group of Karabutov from Moscow State University proposed a combined array that can be used in both imaging modalities. However, the proposed design was limited to a scanning system based on a single transducer that is focused into a point at some specific depth (19). This design could only be used for one-dimensional depth profiling, potentially for two-dimensional imaging, even though the design is shown only for a single transducer, but not for three-dimensional tomography. This design remains just an idea several years after the original publication likely because authors themselves realized a number of technical deficiencies limiting usefulness of this system in biomedical applications.

A major drawback of this design is that the array is focused into a line and it will take a long time to acquire complete 2D image of a slice, which is not practical. Moreover, the main problem in the design is that it cannot be used for optoacoustic imaging as described because the laser pulse strikes a strongly absorbing polymer layer and there is no laser pulse delivery directly to the tissue surface. Therefore, even though the paper implies a combined laser ultrasound and optoacoustic system, the proposed array can be used only for laser ultrasound imaging which is similar to the designs developed for laser ultrasound nondestructive evaluation of industrial materials.

Despite years of research effort, there remains an urgent need for the development of imaging technology that can improve the sensitivity of detection, specificity of biomedical diagnostics and characterization of changes that occur during and after therapeutic interventions by providing comprehensive detailed unobstructed high resolution volumetric pictures of biological tissues, organs and bodies. Detection and treatment of breast cancer especially is lacking the needed technologies. The current problems of breast cancer care are numerous (1-5), i.e., a large number (~20%) of breast tumors are missed by x-ray mammography, especially in the dense breast of younger women, (2) about 75% of biopsies are unnecessary, cancers are missed due to insufficient contrast of ultrasound guided biopsy, and a lack of fast and safe functional imaging techniques to assess the effectiveness of anticancer chemotherapy and other therapies. Diagnostic and treatment of many other diseases (atherosclerosis and peripheral vascular diseases, heart disease and stroke, diabetes and burns) and biomedical research (in cancer biology, hematology, neurology and drug discovery and testing) can benefit from the comprehensive 3D tomography system.

While prior art systems may provide a base for the design and development of a clinically viable laser optoacoustic ultrasonic imaging system (LOUIS) (19,20), Previously developed optoacoustic imaging systems and laser ultrasound monitoring systems have limited resolution and sensitivity, have limited field of view, have reduced accuracy of quantitative information, have artifacts associated with projection onto image plane of objects located out of the image plane, and have no capability to provide detailed information on distribution of speed of sound.

Thus, there is a recognized need in the art for an improved three-dimensional tomographic system that overcome these limitations. Particularly, the prior art is deficient in a tomographic system that combines laser ultrasound and laser optoacoustic tomography useful for many biomedical applications such as, but not limited to, cancer detection or screening, monitoring of anticancer therapies, detection and characterization of vascular diseases, monitoring drug distribution, distribution of nanoparticles or contrast agents and physiological and pathological processes. The present invention fulfills this longstanding need and desire in the art.

SUMMARY OF THE INVENTION

The present invention is directed to a laser ultrasonic imaging system. The imaging system comprises means for delivering short pulses of optical energy to an array of ultrasonic emitters comprising optically absorbing elements placed in specific locations configured for efficient conversion of the absorbed optical energy into a short pulses of acoustic energy within a wide band of ultrasonic frequencies. The imaging system comprises means for delivering the short ultrasonic pulses with known amplitude and ultrasonic frequency spectrum through a coupling medium to a volume of interest in a subject at a given time or time zero. The imaging system comprises means for detecting the ultrasonic pulses in multiple positions at or around said volume of interest and measuring one or more parameters of time of propagation, amplitude and ultrasonic frequency spectrum, after the ultrasonic pulses are transmitted through or reflected from the volume of interest using an array of wide-band ultrasonic transducers that convert ultrasonic pulses into electronic signals. The imaging system comprises means for analog amplification and digital recording of the electronic signals and for performing signal processing to remove distortions of electronic signals. The imaging system comprises means for image reconstruction using mathematical tomography algorithms, means for image processing and display and for data transmission and system control.

The present invention also is directed to a dual-modality imaging system. The dual-modality imaging system comprises a first means comprising the laser ultrasonic system described herein configured to generate tomographic images of a volume of interest in a subject body utilizing parameters comprising one or more of the speed of sound, ultrasound attenuation or ultrasound backscattering. The dual-modality imaging system comprises a second means for generating optoacoustic tomographic images of distribution of the optical absorption coefficient in the subject body utilizing parameters of the absorbed optical energy density or various quantitative parameters that can be derived from the optical absorption.

The present invention is directed further to a imaging method for increasing contrast, resolution and accuracy of quantitative information obtained within a subject. The method comprises the steps of producing a laser ultrasound or laser optoacoustic image of an outline boundary of a volume of interest within the subject using the dual-modality imaging system described herein. A spatially or temporally coregistered image of speed of sound and/or an image of ultrasonic attenuation within the outlined volume boundary is generated from information contained in the laser ultrasound or laser optoacoustic image and a spatially or temporally coregistered optoacoustic image is generated based on absorbed optical energy using an algorithm of the image reconstruction that employs distribution of the speed of sound and/or ultrasound attenuation within the outlined volume boundary.

The present invention is directed further still to a laser optoacoustic ultrasound imaging system (LOUIS). The LOUIS imaging system comprises a dual laser source switchable between a laser ultrasonic mode and a laser optoacoustic mode, where the laser source is configured to emit either short optical pulses with high repetition rate for the illumination of the ultrasonic emitters in the ultrasonic mode or short optical pulses with lower repetition rate but higher pulse energy for the illumination of the volume of interest in the optoacoustic mode. The LOUIS imaging system comprises an imaging module comprising one or more ultra-wide-band ultrasonic transducers configured to detect, through a coupling medium, optoacoustic and ultrasonic signals propagated as transient pressure waves from the volume of interest within a subject body. The LOUIS imaging system comprises means to rotate and/or translate the imaging module relative to the volume of interest in the subject body to create multiple pressure waves, said means computer controllable or manually controllable. The LOUIS imaging system comprises means for processing the detected laser optoacoustic and laser ultrasonic signals and for reconstructing processed signals into one or more of anatomical and functional/molecular images of the volume of interest in the subject body. The present invention is directed to a related LOUIS imaging system further comprising means for displaying the one or more images or superimposed coregistered images of the subject body or the volume of interest therein.

The present invention is directed further still to a method for imaging a subject's body or a volume of interest therewithin. The method comprises positioning the subject body within or proximate to the imaging module of the laser optoacoustic ultrasound imaging system described herein, delivering a laser-generated pulses of ultrasonic energy to a volume of interest in the subject body and detecting the transmitted or reflected ultrasonic pressure waves while measuring one or more parameters comprising a difference between the time of emission and a time of arrival, a difference between emitted amplitude and detected amplitude, and a difference between ultrasonic frequency spectrum of emitted and detected ultrasonic pulses. Then delivering a laser-generated pulse of optical energy is delivered to a volume of interest in the subject body and the ultrasonic pressure waves generated through optical absorption inside the subject body are detected while measuring one or more parameters comprising a time of arrival relative to a time of generation, an amplitude of detected optoacoustic signals, and an ultrasonic frequency spectrum of detected optoacoustic signals. The subject body or volume of interest therein is scanned with a detecting array of ultrawide-band ultrasonic transducers by repeating steps the previous steps at multiple positions around the subject body or volume of interest while simultaneously scanning the sources of optical energy and sources of ultrasonic energy such that relative position of the detecting array of ultrasonic transducers and the sources of optical or ultrasonic energy can change or remain constant during the scans. processing the detected ultrasonic signals are processed to remove distortions of detected signals and one or more volumetric images are reconstructed via mathematical tomography algorithms using data of the processed signals.

Other and further aspects, features, and advantages of the present invention will be apparent from the following description of the presently preferred embodiments of the invention given for the purpose of disclosure.

BRIEF DESCRIPTIONS OF THE DRAWINGS

So that the matter in which the above-recited features, advantages and objects of the invention, as well as others that will become clear, are attained and can be understood in detail, more particular descriptions of the invention briefly summarized above may be had by reference to certain embodiments thereof that are illustrated in the appended drawings. These drawings form a part of the specification. It is to be noted, however, that the appended drawings illustrate preferred embodiments of the invention and therefore are not to be considered limiting in their scope.

FIG. 6 is a table of Gruneisen parameters for liquids and solids with high thermal expansion and high speed of sound.

Figure 14:
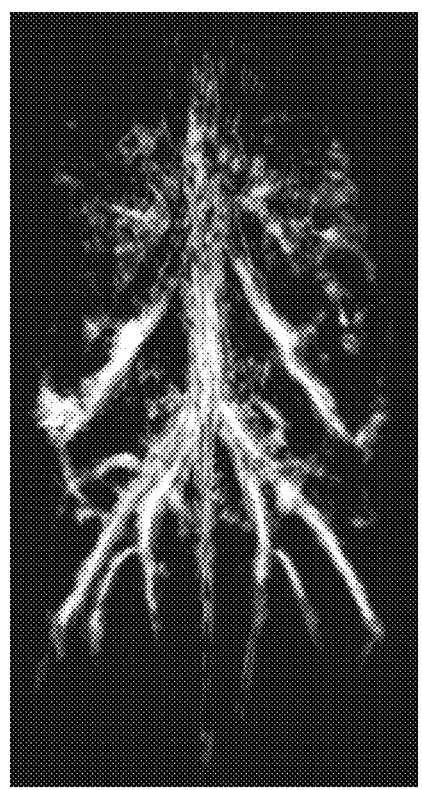

FIG. 14 2D projection of a 3D LOUIS image of an animal body vasculature.

Figure 15:
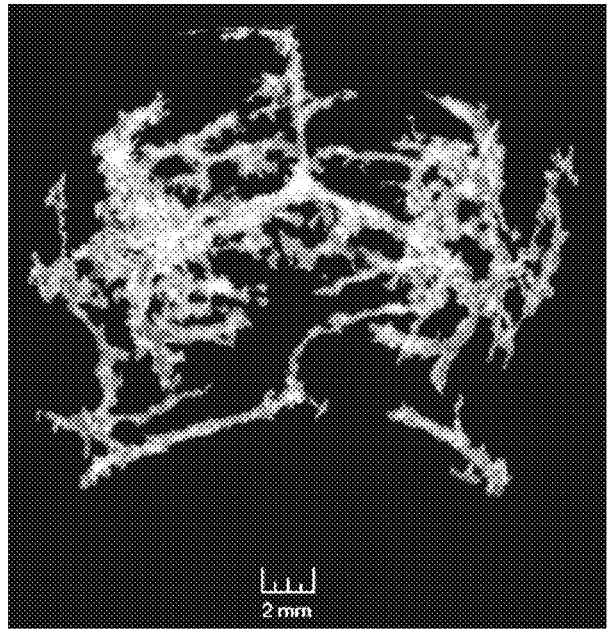

FIG. 15 is an optoacoustic image of brain vasculature in a live mouse.

FIGS. 16A-16C show 2D projections of 3D optoacoustic images using contrast agents of a breast tumor (FIG. 16A) before (FIG. 16B) and after injection of GNR-PEG-Herceptin (FIG. 16C).

Figure 17A:
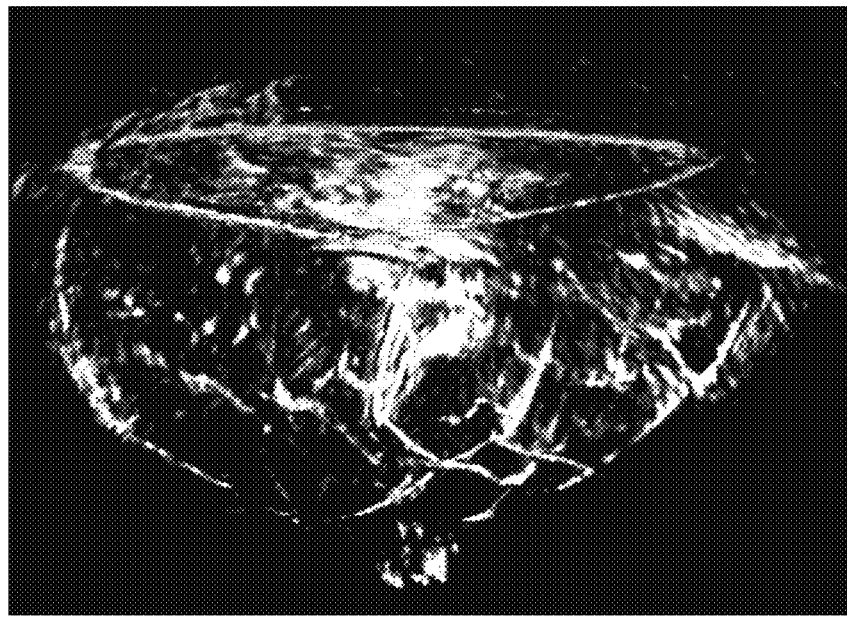
Figure 17B:
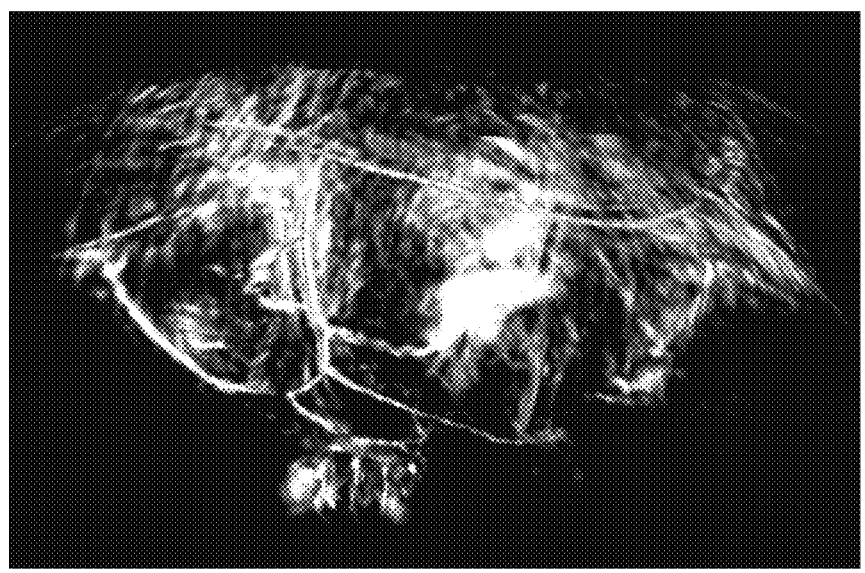

FIGS. 17A-17B are 3D laser optoacoustic images of breasts acquired and reconstructed with LOUIS-3D.

FIG. 18 illustrates the optoacoustic image reconstruction algorithm.

Figure 19A:
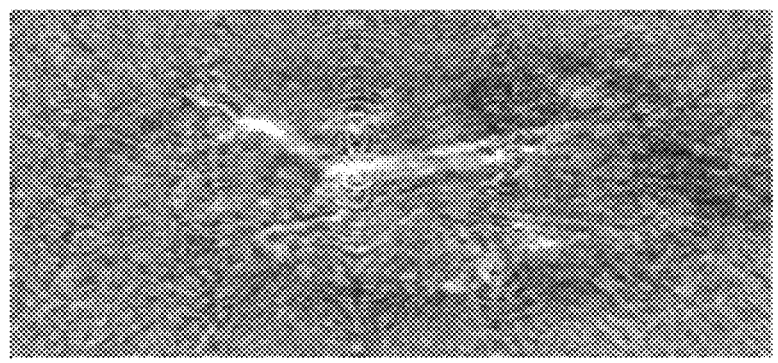
Figure 19B:
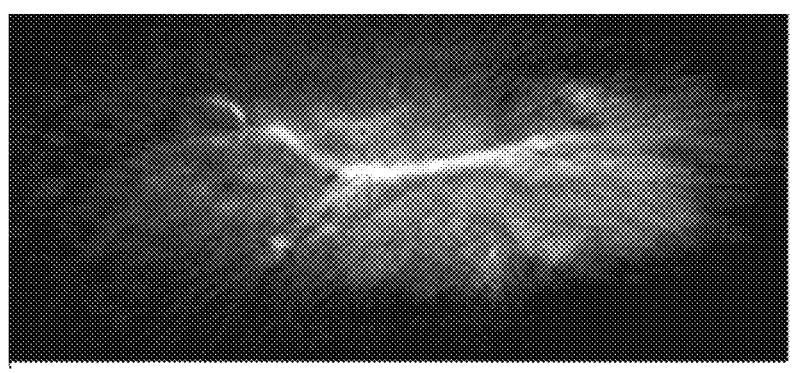

FIGS. 19A-19B are optoacoustic images of a mouse vasculature reconstructed with a standard filtered backprojection algorithm (FIG. 19A) and with a filtered backprojection algorithm (FIG. 19B) as detailed in FIG. 18.

Figure 20A:
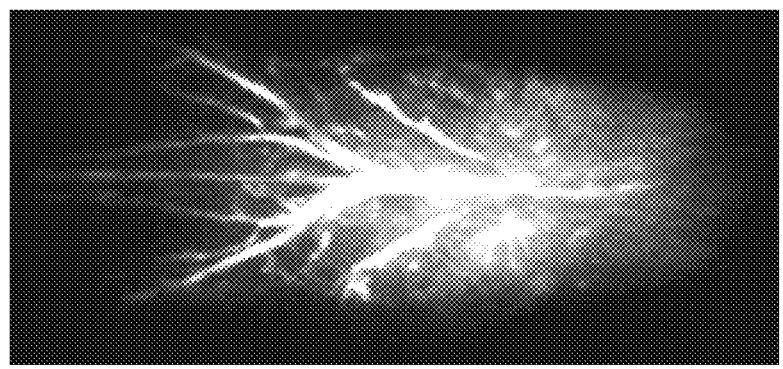
Figure 20B:
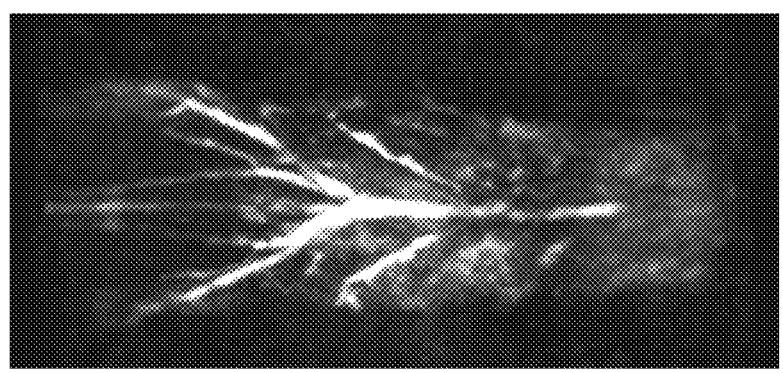

FIGS. 20A-20B are images reconstructed using a filtered backprojection algorithm and the entire set of measured signal data (FIG. 20A) and using an iterative algorithm taking only ¼ portion of the data set (FIG. 20B).

DETAILED DESCRIPTION OF THE INVENTION

As used herein in the specification, "a" or "an" may mean one or more. As used herein in the claim(s), when used in conjunction with the word "comprising", the words "a" or "an" may mean one or more than one.

As used herein "another" or "other" may mean at least a second or more of the same or different claim element or components thereof. Similarly, the word "or" is intended to include "and" unless the context clearly indicates otherwise. "Comprise" means "include."

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, the term "computer" or "computer system" refers to any networkable tabletop or handheld electronic device comprising a memory, a processor, a display and at least one wired or wireless network connection. As is known in the art, the processor is configured to execute instructions comprising any software programs or applications or processes tangibly stored in computer memory or tangibly stored in any known computer-readable medium.

As used herein, the term "subject" refers to a human or other mammal or animal or to any portion or body part thereof on which imaging, for example, laser optoacoustic ultrasound imaging, may be performed.

In one embodiment of the present invention there is provided a laser ultrasonic imaging system, comprising a) means for delivering short pulses of optical energy to an array of ultrasonic emitters comprising optically absorbing elements placed in specific locations configured for efficient conversion of the absorbed optical energy into a short pulses of acoustic energy within a wide band of ultrasonic frequencies; b) means for delivering said short ultrasonic pulses with known amplitude and ultrasonic frequency spectrum through a coupling medium to a volume of interest in a subject at a given time or time zero; c) means for detecting said ultrasonic pulses in multiple positions at or around said volume of interest and measuring one or more parameters of time of propagation, amplitude and ultrasonic frequency spectrum, after said ultrasonic pulses are transmitted through or reflected from the volume of interest using an array of wide-band ultrasonic transducers that convert ultrasonic pulses into electronic signals; d) means for analog amplification and digital recording of said electronic signals; e) means for performing signal processing to remove distortions of electronic signals; f) means for image reconstruction using mathematical tomography algorithms; g) means for image processing and display; h) means for data transmission and system control.

In this embodiment system may be configured to produce in real time at a video rate two-dimensional images of thin tissue slices based on measured parameters of the speed of sound, ultrasound attenuation or ultrasound backscattering. Also, in this embodiment system may be configured to produce three-dimensional images of the volume of interest in a subject body based on measured parameters of the speed of sound, ultrasound attenuation or ultrasound scattering. In an aspect of this embodiment the means for detecting the ultrasonic pulses comprises a hand-held probe configured for acquisition, reconstruction and display of real-time two-dimensional or three-dimensional images.

In another embodiment of the present invention there is provided a dual-modality imaging system, comprising a) first means comprising the laser ultrasonic system of described supra configured to generate tomographic images of a volume of interest in a subject body utilizing parameters comprising one or more of the speed of sound, ultrasound attenuation or ultrasound backscattering; and b) second means for generating optoacoustic tomographic images of distribution of the optical absorption coefficient in the subject body utilizing parameters of the absorbed optical energy density or various quantitative parameters that can be derived from the optical absorption.

In this embodiment the first generating means may comprise laser-generated ultrasound and the second generating means may comprise laser-generated optoacoustics, both of said first and second means comprising an ultrawide-band ultrasonic transducer array positioned for acoustic detection of transient pressure waves resulting from delivery of the laser-generated ultrasound and the laser-generated optoacoustics. Particularly, the images may be generated by the laser-generated ultrasound are tomographic images of tissue anatomy, morphology and structure. In an aspect of this embodiment the images may be generated by the laser-generated optoacoustics are tomographic images of tissue functional molecules such as hemoglobin, oxyhemoglobin, water, lipids, proteins and other molecules of biomedical interest. In another aspect the images may be generated by the laser-generated optoacoustics are tomographic images of proteins, nucleic acids, enzymes and other molecules comprising tissue of biomedical interest targeted with exogenous contrast agents or images of a spatial distribution of the exogenous contrast agents, where the contrast agents increasing contrast or characterizing molecules, cells or tissues. Representative examples of exogeneous contrast agents are optical, optoacoustic, acoustic ultrasonic or dual optoacoustic-ultrasonic contrast agents and the contrast agents are either molecules or nanoparticles. In all embodiments and aspects of the present invention the images may be spatially coregistered or temporally coregistered.

In yet another embodiment of the present invention there is provided a imaging method for increasing contrast, resolution and accuracy of quantitative information obtained within a subject, comprising the steps of a) producing a laser ultrasound or laser optoacoustic image of an outline boundary of a volume of interest within the subject using the dual-modality imaging system described supra; b) generating a spatially or temporally coregistered image of speed of sound and/or an image of ultrasonic attenuation within the outlined volume boundary from information contained in the laser ultrasound or laser optoacoustic image; and c) generating a spatially or temporally coregistered optoacoustic image based on absorbed optical energy using an algorithm of the image reconstruction that employs distribution of the speed of sound and/or ultrasound attenuation within the outlined volume boundary.

In yet another embodiment of the present invention there is provided a laser optoacoustic ultrasound imaging system (LOUIS), comprising a) a dual laser source switchable between a laser ultrasonic mode and a laser optoacoustic mode, said laser source capable to emit either short optical pulses with high repetition rate for the illumination of the ultrasonic emitters in the ultrasonic mode or short optical pulses with lower repetition rate but higher pulse energy for the illumination of the volume of interest in the optoacoustic mode; b) an imaging module comprising one or more ultrawide-band ultrasonic transducers configured to detect, through a coupling medium, optoacoustic and ultrasonic signals propagated as transient pressure waves from said volume of interest within a subject body; c) means to rotate and/or translate said imaging module relative to the volume of interest in the subject body to create multiple pressure waves, said means computer controllable or manually controllable; d) means for processing said detected laser optoacoustic and laser ultrasonic signals and reconstructing processed signals into one or more of anatomical and functional/molecular images of the volume of interest in the subject body. The present invention is directed to a related laser optoacoustic ultrasound imaging system further comprising means for displaying the one or more images or superimposed coregistered images of the subject body or the volume of interest therein. Further to this embodiment the LOUIS imaging system comprises means for displaying the one or more images or superimposed coregistered images of the subject body or the volume of interest therein.

In both embodiments laser optoacoustic illumination may be performed in orthogonal mode, backward mode forward mode relative to the subject body or the volume of interest therein. Also, laser ultrasonication may be performed in transmission or forward mode or in reflection or backward mode relative to the subject body or the volume of interest therein or in a combination of the modes. In addition the laser wavelength may be about 532 nm to about 1064 nm. Furthermore, the one or more ultrawide-band ultrasonic transducers may be configured to detect ultrasonic signals with no or minimal reverberations. Further still the transducer array may be interchangeable for acquisition of various types of images in order to achieve greater contrast, resolution, or quantitative accuracy of either optoacoustic or ultrasonic images or both.

Also, in both embodiments the means for processing and reconstructing said detected ultrasonic signals comprises one or more of electronic amplifiers with time-gain-control circuits; multichannel analog-to-digital-converter with a field programmable gate array; and imaging module design and tomography algorithms configured to reconstruct quantitatively accurate volumetric images.

In one aspect of these embodiments the rotating means may be configured to rotate the imaging module, wherein the detecting array of transducers comprises an arc-shaped array or linear flat array or combination of said array shapes comprising small ultrawide-band ultrasonic transducers with wide angular directivity. In another aspect the translating means may be configured to translate said imaging module, wherein the detecting array of transducers comprises an arc-shaped array or linear flat array or combination of said array shapes comprising finite size ultrasonic transducers with narrow angular directivity. In addition, in these embodiments and aspects, the imaging module comprises a hand-held probe configured for acquisition, reconstruction and display of real-time two-dimensional or three-dimensional images.

In yet another embodiment of the present invention there is provided a method for imaging a subject's body or a volume of interest within, comprising the steps of a) positioning the subject body within or proximate to the imaging module of the laser optoacoustic ultrasound imaging system described supra; b) delivering a laser-generated pulses of ultrasonic energy to a volume of interest in the subject body; c) detecting the transmitted or reflected ultrasonic pressure waves while measuring one or more parameters comprising a difference between the time of emission and a time of arrival, a difference between emitted amplitude and detected amplitude, and a difference between ultrasonic frequency spectrum of emitted and detected ultrasonic pulses; d) delivering a laser-generated pulse of optical energy to a volume of interest in the subject body; e) detecting the ultrasonic pressure waves generated through optical absorption inside the subject body while measuring one or more parameters comprising a time of arrival relative to a time of generation, an amplitude of detected optoacoustic signals, and an ultrasonic frequency spectrum of detected optoacoustic signals; f) scanning the subject body or volume of interest therein with a detecting array of ultrawide-band ultrasonic transducers by repeating steps b) to e) at multiple positions around the subject body or volume of interest while simultaneously scanning the sources of optical energy and sources of ultrasonic energy such that relative position of the detecting array of ultrasonic transducers and the sources of optical or ultrasonic energy can change or remain constant during the scans; g) processing the detected ultrasonic signals to remove distortions of detected signals; and h) reconstructing one or more volumetric images via mathematical tomography algorithms using data of the processed signals.

In this embodiment the pulse of optical energy may have a duration shorter than the time of pressure wave propagation through the distance in the subject body or volume thereof equal to a desired spatial resolution. Also, the other energy may be electromagnetic energy with a wavelength of about 1 nm to about 1m. In addition the one or more volumetric images may be three-dimensional images of the volume of interest or of the subject body, or may be two-dimensional slices through the three-dimensional volume of interest or even one-dimensional profiles of molecules of interest within the volume. Furthermore at least one volume of interest may be a tumor, a lymph node, a vascular circulation network, or a brain. Further still the laser ultrasound or laser optoacoustic images may provide a feedback for guidance of therapeutic treatments or surgical interventions.

In this embodiment the scanning step may comprise a) scanning the whole subject subject body with a first array of ultrasonic transducers in a rotational configuration to determine at least one volume-of-interest and its characteristics related to absorbed optical energy; b) replacing the first array with a second array of ultrasonic transducers in a translational configuration; and c) scanning through said at least one volume-of-interest with a high resolution sufficient to acquire quantitative information related to distribution and concentration of functional molecules therein. Also the step of delivering pulsed optical energy may be performed at multiple wavelengths of light, whether in sequence or toggling.

Provided herein is a dual- or multi-modality three-dimensional (3D) tomography or imaging system that comprises laser optoacoustic tomography (OAT) and laser ultrasound tomography (UST). This three-dimensional tomography system provides comprehensive biomedical information about a portion of the subject body under examination. More specifically, the system employs principles of laser ultrasound and laser optoacoustic imaging to reconstruct three-dimensional distributions showing anatomical structures of a portion of the subject body under examination, molecular composition and distribution of functionally important molecules in biological tissues of the subject body. All tomographic images are correlated and spatially coregistered. For dynamic processes that change over time, temporal coregistration can be obtained so that anatomical and molecular images can be superimposed at a given time. Furthermore, optoacoustic images of the outline of the subject body, i.e., the skin, are used to inform more accurate reconstruction of ultrasonic images, and the ultrasonic images in turn, inform more accurate reconstruction of optoacoustic images of the volumetric distributions of molecules of interest.

The instant invention describes the full set of properties of the layers of the materials for the most effective generation of ultrawide-band ultrasound with laser pulses, not discussed in the prior art. They are a very small thickness of the layer of the laser illuminated material measured in microns, a very strong optical absorption of a selected laser wavelength so that sufficient optical energy can be absorbed even within the very small thickness of the layer, and a large thermo-acoustic efficiency parameter $$\Gamma = \frac{c_0^2 \beta^*}{C_p},$$

for the material of the illuminated layer or large thermoacoustic efficiency (often called Gruneisen parameter) of the medium surrounding the laser-illuminated layer. The large $\Gamma\beta$ can be achieved through a large thermoelastic expansion coefficient, $\beta$, and fast (high) speed of sound, and small heat capacity. These properties must be combined in one design to achieve maximum efficiency.

This invention provides a three dimensional tomography system that acquires and displays comprehensive volumetric information about biomedical object of interest, for example, tissue, cells, subject body or organ, with high contrast and high resolution. The depth at which this information can be obtained under optimal imaging conditions is up to 6-7 cm, which is significantly greater than the depth of pure optical imaging with similar resolution. With this depth of imaging, biomedical objects such as human breast as large as 14 cm can be visualized. The information that can be obtained from LOUIS images includes anatomical, i.e., structural or morphological, information and functional information about hemoglobin distribution in blood and the level of oxygenation in the hemoglobin. LOUIS also can provide images of biomedical objects with molecular specificity, i.e. images of distribution of molecules of interest.

If these molecules do not have sufficient intrinsic optical absorption in the wavelength range of laser pulses utilized in LOUIS, then contrast agents targeted to those molecules through specific molecular probes or other high affinity vectors can be used. LOUIS contrast agents are molecules, nanoparticles, nanobubbles or combination thereof. The optoacoustic ultrasonic contrast agents are in general those probes that have high optical absorption and/or utilize high thermoacoustic efficiency and/or have strong capability to scatter, reflect or absorb ultrasonic waves or change speed of sound in the said biomedical object or any substance or structure that can be used to enhance contrast of LOUIS images.

Ultrasound pulses for 3D biomedical imaging can be generated by short laser pulses, which gives significant advantages to the system performance and image contrast and resolution. Specifically, a special ultrasound generating medium, which under illumination of a short laser pulse produces clean smooth short non-reverberating pulses of ultrasound, is utilized. This produces either monopolar pressure pulses (so called Delta pulses of ultrasound (6)) or bipolar pressure pulses, if an application requires such pulses. Short nonreverberating ultrasound pulses produced by laser pulses or by pulses of electromagnetic energy, in general, will results in greater resolution and contrast of 3D ultrasonic images. For example, a standard piezoelectrically generated ultrasound pulse has 3-4 reverberations, so if produced with 12 MHz central frequency will have envelope frequency 3-4 MHz effectively.

Therefore, the axial resolution of ultrasonic images is defined by the frequency of an envelope of that reverberating ultrasonic pulse and be at least 3-4 times lower than that of 3D ultrasound image produced with laser pulses. Short nanosecond laser pulses can generate pulses of ultrawide-band ultrasound with frequencies from low (tens of kHz) to high (tens of MHz). These ultrawide-band ultrasound pulses are very beneficial for ultrasound imaging since they is effectively scattered and attenuated by variety of biomedical object structures (large such as tumors or large vessels to small such as microvessels to microscopic such as cells and even subcellular components. Biomedical objects (tissue and cells) can absorb and scatter certain frequencies of ultrasound while other frequencies can pass said objects undistorted. Therefore, spectroscopic analysis of laser ultrasonic signals in terms of their frequency spectra can reveal useful diagnostic information. Three dimensional images obtained with laser ultrasound such as the image ultrasound attenuation, the image of ultrasound scattering/deflection and the image of distribution of ultrasound velocity (most frequently called speed of sound) are also very rich of information that can be used by physicians and biomedical researchers for characterization and differentiation of biomedical objects (tissues, cells, organs etc).

LOUIS utilizes short nanosecond laser pulses for generation of short pressure pulses which propagate as ultrawide-band ultrasound in biomedical objects. LOUIS operates in two modes, Laser Ultrasonic and Laser Optoacoustic. Images of both modes can be fully coregistered, correlated and superimposed since they are collected with one and the same set or array of ultrasonic transducer detectors. In general, LOUIS can utilize illumination with any optical wavelength or even any wavelength of electromagnetic energy and any sequence or duration of pulses of said electromagnetic energy. But short, about 1 ns to about 20 ns laser pulses in the near-infrared spectral ranging from about 650 nm to about 1250 nm are preferred for imaging with LOUIS.

In the laser ultrasonic mode, the laser pulses illuminate a special medium placed outside of the biomedical object of interest, so that these short pulses of ultrasound enter the biomedical object of interest, propagate through the object of interest and interact with the ultrasonic transducers for purposes of their detection. A laser wavelength selected for generation of laser ultrasound pulses is usually chosen to be strongly absorbed in the external special medium and then effectively converted into heat and pressure, with high-pressure generation efficiency being the ultimate goal. The detected ultrasonic pulses represent electronic signals that, after signal processing, e.g., filtering, conditioning, analysis etc., are used for further reconstruction of volumetric ultrasonic images using mathematical algorithms. LOUIS can be used to reconstruct at least three types of ultrasonic images: the image of the speed of sound, the image of ultrasonic attenuation and the image of ultrasonic reflection (deflection, scattering).

In the laser optoacoustic mode the laser pulses illuminate the biomedical object of interest itself, propagate through the object and interact with the object of interest, so that the energy of these optical pulses can be absorbed by its components and constituents and converted into heat and simultaneously thermal pressure, which then propagates as ultrasound and interacts with said ultrasonic transducers for purposes of their detection. The wavelength of the laser pulses is selected to propagate to a desirable depth in the object, e.g., tissue, and become preferentially absorbed by specific molecular constituents of interest: hemoglobin, oxy-hemoglobin, water, lipids, melanin and other endogenous molecules of interest or exogenous molecules or particles or probes of exogenous contrast agent.

The detected ultrawide-band ultrasonic pulses represent electronic signals, which after signal processing, i.e., analysis, filtering, conditioning, etc, are used for further reconstruction of volumetric optoacoustic images using mathematical algorithms. The optoacoustic images represent distribution of absorbed optical energy at a selected wavelength or a collection of multiple wavelengths, and after normalization to distribution of the optical fluence can represent distribution of the optical absorption coefficient in the biomedical object. After image post-processing the optoacoustic images can be converted into a number of quantitative volumetric images, including, but not limited to. the following five types: the image of the total hemoglobin (THb), the image of hemoglobin oxygenation (SO2), the image of water distribution (H2O), and the image lipid/fat distribution (Lipid) and the molecular image of distribution of a specific molecule of interest.

In order to transmit ultrasonic and laser (optical) pulses to the biomedical object, then detect ultrasonic (acoustic pressure) pulses from the object and reconstruct the laser ultrasound and laser optoacoustic images using LOUIS, usually a coupling medium is required. For better image quality the following properties of the coupling medium is desired: good optical transparency in the wavelength range of laser pulses used for illumination, good ultrasonic acoustic transparency in the frequency range of ultrawide-band ultrasonic pulses used for imaging, good matching of the optical refraction index to the tissue of the biomedical object and good acoustic impedance matching to the tissue of said biomedical object. In addition, it will help to image deeper and with less noise and artifacts, if the coupling agent makes the tissue of the biomedical object optically clear. Skin clearing media have been proposed and developed for increased optical transparency of skin for better quality of optical images. However, as disclosed herein, optical clearing agents can improve quality, fidelity and contrast of laser optoacoustic images and laser ultrasonic images.

Many types of lasers and other pulsed sources of electromagnetic energy can be used for LOUIS. The most preferred lasers are those tunable in the near-infrared spectral range and simultaneously robust for biomedical applications, such as Nd:YAG pumped Ti:Sapphire laser and solid state diode laser matrices.

The ultrasonic transducers (detectors) can be made of various materials and utilize various technologies. The preferred materials include polymers, crystals, ceramics, and composites. The types of ultrasound (pressure) detectors include piezoelectric transducers, capacitive micromachined ultrasonic transducers (CMUT), optical beam deflection transducers, fiberoptic sensors, optical interferometers and microphones. The most preferred detectors for LOUIS are those that possess higher sensitivity and simultaneously can detect ultrasound within an ultrawide band of ultrasonic frequencies.

Signal processing in LOUIS includes analysis of signal profiles, signal amplitudes and spectrum of signal frequencies. Spectra, e.g., Fourier spectra, of laser ultrasound signals propagated through the biomedical object can be analyzed to reveal properties of tissues important for biomedical diagnostics. Such spectra of laser optoacoustic signals generated by optically induced acoustic sources within the biomedical object and propagated through the biomedical object also can be analyzed to reveal properties of tissues important for biomedical diagnostics.

Analysis of noise in the system can help to filter the noise and improve contrast of images. Whether the noise is white and noncorrelated or the noise is correlated between various detectors or transducers or transducer positions around the object, mathematical methods exist and can be chosen to provide the best filtering of the signals from noise. In general, signal processing for LOUIS is designed to reverse the so called system transfer function, i.e. all distortions that introduced into the detected ultrasonic signals by the system components, such as lasers, detectors and analog and digital electronics. The goal is to obtain electronic signals with properties as close as possible to the intrinsic pressure or ultrasound signals.

One specific method of signal processing is preferred due to the accuracy of quantitative information provided by the volumetric optoacoustic images. This method provides for volumetric image reconstruction based on signal deconvolution using the Curvelet transform, a two-dimensional wavelet transform, known in the art, for filtering optoacoustic and ultrasonic signals. The most desirable property of wavelets is their capability to filter signals simultaneously in time and frequency domains, thus providing great separation of useful signals and noise that appear in the same frequency range. Thus provided herein is an algorithm for laser ultrasonic and laser optoacoustic image reconstruction in 3D using the Curvelet deconvolution method. Also provided are algorithms aimed at total variance minimization that can be beneficial for laser ultrasound and laser optoacoustic tomography.

Three dimensional tomography images are much more quantitatively accurate compared with two-dimensional images due to collection of complete sets of data and to rigorous reconstruction algorithms based on information about the object collected from various angles and positions in the 3D space. The ultimate image would be a 3D image obtained in real time, i.e. obtained within such a short period of time when important biomedical conditions of the object of interest could not change. Typically, acquisition of 10-30 images per second in biomedical applications is sufficient to be considered as real-time monitoring. One image per second also is acceptable for monitoring kinetics and dynamics of biological processes. So, the most important are designs in which data are collected rapidly, while image reconstruction can be done later. Alternatively, image reconstruction in real time brings practical convenience in biomedical imaging, allowing the doctor to make an immediate decision in the presence of a patient. Thus, the present invention provides reconstruction of laser ultrasonic and laser optoacoustic images with hardware and algorithms operating in real time with the use of the modern and advanced computer power capabilities. Field Programmable Gate Arrays (FPGA) microprocessors are most effective for signal processing, Graphical (multicore) processor units (GPU) are most effective for image reconstruction, while the Central Processing Unit (CPU) of a computer is the most effective for display of images and system controls.

Thus, LOUIS has multiple biomedical applications including but not limited to, cancer detection or screening, including detection of cancer in the lymph nodes and metastatic tumors, cancer diagnostics, monitoring effects of anticancer therapy and aggressiveness of a cancer, detection and characterization of vascular diseases, such as, cardiovascular disease, stroke, peripheral vascular disease, diseases that result in the damage of microvasculature, e.g., diabetes, atherosclerosis, monitoring circulation and its functions, anatomical, functional and molecular characterization of various tissues and health conditions, functional imaging of blood distribution and its oxygen saturation levels. Other biomedical applications include molecular imaging of various molecular targets of diseases and otherwise abnormal tissues, monitoring kinetics of drug distributions and biodistribution of nanoparticles and other contrast agents, monitoring physiological and pathological processes in the animal or human subject body, monitoring trauma, burns and otherwise damaged tissues and the process of its recovery after treatment.

Particularly, the combined imaging system comprises the following advantages:

LOUIS-Combined 3D Optoacoustic/Ultrasonic Imager

Laser optoacoustic ultrasonic imaging system is a 3D tomography system for the comprehensive characterization of biomedical objects. The 3D tomography system creates a spherical surface of virtual transducers by rotation of an arc-shaped ultrasonic array around the object of interest with computer-controlled illumination from multiple positions, which permits the most beneficial distribution of light in the object. The time of the entire 3D image acquisition can be as short a few seconds, but may be extended for several minutes for the benefit of image quality in the object has low contrast. The LOUIS system components comprise electronics hardware, firmware, software and custom designed wavelength tunable lasers. One laser has relatively low pulse energy of about 0.1 to about 2 mJ, and a high repetition rate of laser pulses (1-5 kHz) used to generate ultrasound pulses outside the subject body under examination. The second laser has much higher pulse energy, up to 250 mJ, a relatively low repetition rate (10-20 Hz) and a wavelength tunable in the near-infrared spectral rage, with capability to electronically switch or toggle the illumination wavelengths, for example, 1064/800 nm, 1064/757 nm, for functional optoacoustic imaging.

Use of Laser-Induced Ultrasound for UST Conventional electrical generation of ultrasound was replaced with laser-induced ultrasound (LU) for transmitting short ultrasound pulses to the breast and thereby achieving three-fold improved UST image resolution and greater sensitivity. LU is emitted by a thin layer of black polydimethylsiloxane (PDMS) and polymethyl methacrylate (PMMA) filled with absorbers polymer embedded with highly concentrated absorbers. Strong absorbers are, but not limited to, carbon nanotubes, strongly absorbing in the near-infrared and having high thermal expansion coefficient. This thin layer is illuminated by pencil beams of short (8 ns) laser pulses from Nd:YAG laser. To decrease the data acquisition time for laser ultrasound imaging, a diode laser can be used with pulse repetition rate of about 1-5 KHz, pulse energy of about 1-2 mJ and pulse duration of 1-3 ns. As a result of strong optical absorption thermal pressure is generated by point sources resulting in spherical ultrasonic waves with ultrawide bandwidth from about 50 KHz to about 30 MHz. The first application of LU was performed in phantoms to obtain fully 3D UST images.

Novel Optoacoustic/Ultrasonic Transducer Array as LOUIS Imaging Probe

Current commercial medical ultrasonic transducers provide spatial resolution two-three times lower than potentially attainable with a given ultrasound frequency. The invented new technology of ultra-wide band transducers we teach here improves sensitivity to enable the optoacoustic imaging of tumors at significant depth up to 6-7 cm, i.e. through large biomedical objects such as entire breast, and also improves resolution of ultrasound images. With novel transducer materials employed in our probes we achieved a very challenging goal: increase sensitivity of detection and simultaneously increase the detection bandwidth.

Advanced 3D Image Reconstruction Methods

New image reconstruction algorithms are developed and implemented for forming images that depict the distribution of the absorbed optical energy density within biomedical objects (live tissues), which can reveal the location of cancerous lesions or other abnormalities that have elevated blood content. Both analytic and iterative reconstruction algorithms are developed and quantitatively evaluated for performance. These algorithms compensate for important physical factors such as the impulse response of the transducer, stochastic and acoustic noise, and finite sampling effects.

I. Dual Mode Image Reconstruction and Coregistration of 3D UST with 3D OAT

In addition to recording optoacoustic signals for use in OAT, the developed 3D imager (LOUIS) is capable of operating in 3D laser UST mode. This enables a novel 3-step method for image reconstruction and processing, which results in significantly higher contrast and resolution of coregistered images. At the first step, we acquire data is acquired and an optoacoustic image or ultrasonic image of the outline of the subject body part under examination is reconstructed. This permits accurate separation of the two domains: subject body part under examination and surrounding volume of the coupling agent. At the second step, data are acquired and image reconstruction methods are implemented for forming images that depict the 3D speed-of-sound (SOS), attenuation, and reflectivity distributions in the portion of the subject body under examination, outlined and defined on the image obtained in the first step.

Therefore, the image of the first step informs a more accurate reconstruction of the image obtained in the second step. At the third step, a volumetric optoacoustic image of the subject body under examination is acquired and reconstructed using information contained in the image obtained in step 2. For example, an image of the speed of sound distribution can be used to correct the time of arrival of optoacoustic signals and thus reconstruct more accurate optoacoustic images. In general, the image providing anatomical/structural information can inform more accurate reconstruction of optoacoustic or functional images. The two types of images (anatomical and functional) are complementary. This is achieved by developing specialized image reconstruction algorithms that utilize boundary conditions and regularization constrains determined from images reconstructed in the previous step.

Preferably, the combined imaging system comprises the physical structure, methods utilized during imaging and the hardware, software and algorithms described below.

Dual-Modality Laser Optoacoustic/Ultrasonic 3D Tomography Imager

The design of the imaging module (see FIGS. 3A-3B) and its components improves, extends and significantly enhances of previously developed preclinical 3D OAT imager (21). The imaging module provided herein, contains a 128 element ultrasound detector array and 7 optical fiber bundles, 4 of which are used for optical illumination of the biomedical object inside the module and its optoacoustic imaging, and 3 of which are coated with a thin absorbing polymer layer to generate laser ultrasound and acquire different types of ultrasound images (speed of sound, ultrasonic attenuation and ultrasound scattering. This unique design enables three different types of measurements to be acquired during a single imaging study: 1) optoacoustic signals for OAT image reconstruction at different laser wavelengths; 2) deflected or backscattered ultrasound for reconstruction of ultrasonic reflectivity maps; and 3) transmission ultrasound for reconstruction of ultrasonic SOS and attenuation maps. The entire imaging module will rotate in order to collect tomographic measurements that are sufficient for accurate image reconstruction.

The ultrasound array is arc-shaped with radius of 70 mm and angular aperture of 150 deg. The remaining 30 deg opening is used for suspending the biomedical object, such as a breast in prone downward position or a whole small animal. The probe has 128 transducers with lateral dimensions of 1.3 mm×1.3 mm and a pitch of 1.4 mm. The transducers are sensitive within an ultrawide band of ultrasonic frequencies from 100 KHz to 10 MHz and exceptionally sensitive in allowing detection of 1 Pa pressure with signal-to-noise (SNR) of 2.

Another novel component of the imaging system is the use of laser-produced ultrasound (LU) for insonifying the breast, as opposed to traditional electrically produced ultrasound (31). LU is emitted by a thin layer of PMMA polymer with embedded highly concentrated absorbers, for example, carbon nanotubes, strongly absorbing in the near-infrared and having high thermal expansion coefficient. This thin layer is illuminated by pencil beams of short (8 ns) laser pulses from Nd:YAG laser. As a result of strong optical absorption, thermal pressure is generated by point sources resulting in spherical ultrasonic waves with ultrawide bandwidth from ~50 KHz to about 30 MHz. The ultrasonic pulse replicates the shape of the laser pulse, which is smooth and short and has no reverberations typical of electrically generated ultrasound. Of course, very high frequencies above 12 MHz can be lost in propagation through tissues, but 12 MHz pulse without reverberations will produce ultrasound resolution equivalent of reverberating 30-35 MHz pulses.

There are three main advantages of employing Laser Ultrasound (LU) as opposed to electrically (transducer) produced in the dual- or multi-modality imager: 1) better spatial resolution, 2) better contrast/sensitivity, 3) simpler and low noise electronics, that is no transmit/receive switches. Image spatial resolution can be superior because LU produces clean, smooth short pulses of ultrasound, not the typical reverberating pulses of electrically generated ultrasound, which needs to be enveloped for imaging purposes. Image contrast can be enhanced because LU pulses have relatively high intensities and minimum background noise. The system electronics are simplified because they are only used for read-out. This circumvents the need to emit 200 V pulses and then quickly detect microVolt signals. Transmit/receive switches are the main source of noise in the conventional ultrasound systems. For example, a supersensitive amplifier sitting next to a super powerful emitter-amplifier can easily be saturated with noise.

Figure 11A:
FIGS. 11A-11B are 2D projections of three-dimensional optoacoustic images of a mouse skin outline in vivo.
Figure 11B:
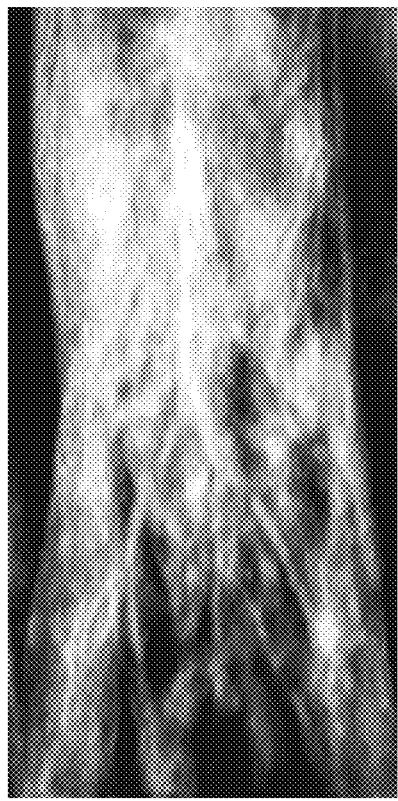

Provided herein are examples of LOUIS images of a whole mouse subject body (see FIGS. 11A-11B). It was demonstrated previously that soft tissue organs, spine, ribs and joints, vasculature or microvasculature can be clearly visualized (21). Microvasculature as small as 50 micron was visualized, even though spatial resolution of the instant system is about an order of magnitude lower.

Thus, the present invention demonstrates the feasibility of a 3D tomographic system design for performing dual-mode laser optoacoustic and laser ultrasonic tomography. LOUIS tomography system creates a spherical surface of virtual transducers by rotation of an arc-shaped ultrasonic array around the object of biomedical interest with computer-controlled illumination from multiple positions, which permits the most beneficial distribution of light in the object. For performing ultrasound tomography, conventional electrical generation of ultrasound for object insonification is replaced with laser-produced ultrasound, thereby, resulting in a three-fold improvement in image resolution. The system development includes electronics hardware, firmware, software and custom design a multi-wavelength tunable laser that enables the capability to electronically switch or toggle the illumination colors, e.g., 1064 nm and one NIR wavelengths in the range from 730 to 850 nm, for optoacoustic imaging. This permits differential imaging of various chromophores, such as hypoxic and oxygenated blood.

OAT image reconstruction algorithms are implemented in LOUIS for forming images that depict the distribution of the absorbed optical energy density within biomedical object, which can reveal the location of abnormal tissues such as cancerous lesions that have elevated blood content. Both analytic and iterative reconstruction algorithms are developed and quantitatively evaluated (see below detailed description of math physics algorithms). These algorithms compensate for important physical factors such as the response of the transducer, stochastic and acoustic noise, and finite sampling effects.

Laser ultrasound tomography utilizes our image reconstruction methods for forming images that depict the 3D speed-of-sound (SOS), ultrasound attenuation coefficient, and reflectivity distributions of biomedical object or organ tissue. These images provide structural information that is complementary to the functional (blood content and oxygenation) information conveyed by the OAT images. Moreover, we teach that the reconstructed SOS and attenuation maps can be utilized to further improve the accuracy of the reconstructed OAT images. This can be achieved through specialized OAT reconstruction algorithms that compensate for variations in the SOS and attenuation distributions.

Computer Modeling

Imager development is based on a comprehensive computer model of 3D OAT and UST. This model includes the following components: 1) calculation of the distribution of absorbed optical energy exponentially decreasing in depth of the breast (32-34), 2) generation of optoacoustic signals, 3) generation of LU for UST imaging, and 4) calculation of profiles of detected signals taking into account the geometry of each transducer element, i.e., directivity diagram of each element, and sensitivity of piezoelectric detectors as a function of the ultrasonic frequency, i.e., effect of bandwidth (29). Computer-software has been developed previously by the inventors that is utilized for establishing a comprehensive physics-based model of the imager. The hardware design is conducted concurrently with the designs of the image reconstruction algorithms described below, so that they can be informed and refined jointly. The image quality measures used to guide the system refinements are described below.

I. OAT Detection-Sensitivity

The sensitivity of optoacoustic detection depends on the product of 4 parameters: the effective optical fluence acting on the tumor, the optical absorption coefficient of the tumor, the thermoacoustic efficiency $\Gamma$, i.e. the ability of tissue to convert light into ultrasound, and the sensitivity of the piezoelectric transducer (35). Using the experimentally measured sensitivity of our new transducers, about 15 microVolt/Pa, and optical properties of breast tumors and normal tissue previously obtained, one can calculate minimal detectable blood content in a tumor with defined dimensions and depth from the illuminated surface (36). Based on this calculation, the imager is capable of detecting not only tumors with dimensions of about 10 mm regularly found by mammography screening, but also early tumors having a very small size of 3 mm. While the detection sensitivity will degrade with depth, those very small tumors may be detected at a depth of 6-7 cm depending on the density of tumor angiogenesis, which in turn defines optical absorption of the tumors (37-39).

II. OAT Imaging Depth

The anticipated imaging depth of OAT in the breast is about 6 cm for typical 10 mm tumors and about 8 cm for blood vessels dependent on the Hb concentration and their dimensions, i.e. comparable with the imaging depth of high-resolution (12 MHz) breast B-mode ultrasound. Even though breast tumors statistically occur most frequently at the depth of 1-3 cm, herein the maximum depth of detection is about 6 cm due to infrequent occurrence of deep tumors in very large breasts. Having effective optical attenuation in tissue of about 3 times per cm of depth, the optical fluence is attenuated about 729 times before it can reach 6 cm depth. However, system electronics described herein is designed with a dynamic range of 14 bits, which permits simultaneous detection of maximum signals and signal attenuated more than 4 orders of magnitude. Furthermore, ultrasensitive transducers provided herein can detect pressure levels of about 1 Pa with signal-to-noise ratio of about 2 (40,41). A 2 Pa pressure can be detected from a ~1-mm object, e.g. a blood vessel, with the optical absorption coefficient of 10/cm located at the depth of 8 cm from the breast tissue surface illuminated with a near-infrared laser pulse having safe optical fluence of 20 mJ/cm$^2$ (8).

III. Spatial Resolution for OAT and UST

Previously, microvessels as small as 50 micron were visualized in a preliminary design of LOUIS animal imager (21), even though spatial resolution of that system was about an order of magnitude lower. The spatial resolution of the OAT images can be spatially variant, being worse at locations that are near the measurement transducer (6,23). The worst spatial resolution for the OAT image, as measured by the FWHM of a point-source response (42), is 0.5 mm. The resolution of the reflectivity UST image is limited by half the effective wavelength, which results in spatial resolution significantly better than 0.5 mm. The resolution of the SOS and attenuation UST images is largely limited by the density of transmit-receive pairs (i.e., number of tomographic views) and the efficacy of the image reconstruction algorithms. An approximately isotropic spatial resolution of <1 mm is presently demonstrated for LU part of LOUIS (see FIG. 8B).

IV. UST Reconstruction Accuracy

Using well-calibrated phantoms enabled reconstruction of the ultrasonic SOS and attenuation distributions of subcutaneous fat, glandular tissue, and tumor tissue to within 0.2% of their known values. Similar tolerances have been reported in studies of breast UST (13,17,18). The ultrasonic reflectivity image is typically used to reveal tissue interfaces only. LOUIS is capable of detecting not only boundaries but also volumes of structures within the biomedical objects.

V. Data-Acquisition and Image Reconstruction Speeds

The acquisition speed for a full set data with a rotating arc-shaped probe is about 3 minutes and multi-modality data acquisition time to less than a minute with the increased sensitivity of the novel transducers and reduced number of averaged signals. The time for full 3D OAT image reconstruction, using a filtered backprojection algorithm, with resolution of 500 micron is reduced in the present LOUIS software relative to earlier version to about 15-30 sec, depending on the total number of voxels within the reconstructed volume, with application of the reconstruction software based on CUDA code and multi-core graphics processing units (GPUs). Fully 3D image reconstruction of the UST images is accelerated using GPUs with an initial accomplishment of reconstructing images in <10 min.

LOUIS Imager Hardware

I. Transducer Array

The optoacoustic/ultrasonic transducer array provided herein is the primary basis for novelty of the LOUIS imaging module. This critically important system component for hybrid dual-modality imaging must satisfy a number of requirements. The optoacoustic signals contain acoustic frequencies ranging from about 200 kHz to 12 MHz, depending on dimensions of tissue optical heterogeneities in the breast and the laser pulse duration (40). Such ultrasonic waves propagate in tissues with attenuation that may be accounted for and deliver spatially resolved information to the surface of tissue where they can be detected and used for image reconstruction (9). However, undistorted detection of ultrasound comprising such a wide frequency range requires acoustic transducers with an exceptionally wide bandwidth (43-45).

Ideally, an optoacoustic transducer is sensitive to the entire range of acoustic frequencies to detect the small and large tissue structures with resolution of <0.5 mm sufficient for biomedical imaging applications in the depth of tissue. Therefore, new piezoelectric materials are incorporated into the design of the transducer arrays that is part of a specially developed clinical probe. The composition of the piezoelectric material and the design of a matching front layer and backing material plays a major role in determining the bandwidth of the probe. Extensive preliminary tests were performed with two different piezoelectric materials: single crystal PZT ceramics, lead metaniobate-titanate (PMN-PT), modified lead titanate (MPT) as part of 1-3 composites. Results demonstrated significant widening of the bandwidth and absence of reverberations in the novel transducers relative to commercial ultrasonic transducers.

II. Patient Bed and Imaging Module for Breast Imaging

A patient table is constructed that contains an imaging module mounted underneath. The patient lies in the prone position on the examination table with the breast suspended through an opening into an imaging module. In order to minimize motions of the breast in the imaging module, we design an inflatable ring balloon that shapes the breast closer to its natural spherical shape. The height of the table is approximately 45 in, which allows the system operator to visually position the breast within the imaging probe while being seated. No compression is required and the breast is centered in the center of the imaging tank by minor movement of the patient. The imaging tank is filled with warm clean water and appropriate plumbing is included in the design to permit rapid changing of the tank water.

III. Electronics, Firmware, Rotation Stage

The system electronics and computer controls in LOUIS are all upgraded from a prior OAT imager to minimize electronic noises. The rotation stage mechanism is essentially different to the one used in our preclinical imager and it provides more accuracy and capability to perform series of scans in clockwise and anticlockwise directions without loss of home position.

Methods

I. Robust OAT Image Reconstruction Methods

In this component of LOUIS, OAT image reconstruction methods are developed, implemented, and optimized for forming images that depict the 3D distribution of the absorbed optical energy density within breast tissue by use of measurement data recorded by the imager. Two classes of reconstruction methods are developed that permit different trade-offs between data-acquisition time and image reconstruction time.

II. Data-Restoration Methods for Use with Analytic Reconstruction Methods

Analytic OAT reconstruction algorithms, such as filtered backprojection (FBP) algorithms (46), form an image by numerically computing a closed-form mathematical formula. Such methods can be computationally efficient and yield relatively short accelerated reconstruction times, for example, <1 min for a volumetric image. However, they typically require a densely sampled tomographic data set to be acquired, which can extend data-acquisition times. Another shortcoming is that they are based on idealized models that do not compensate for noise, the instrument response, and other complicating factors related to the imaging physics.

The effectiveness of the computationally efficient 3D FBP algorithms was improved by developing novel methods for pre-processing the measured multi-dimensional optoacoustic signals prior to image reconstruction. This process is analogous to what is called "sinogram restoration" in the X-ray CT community. This method has never been utilized for optoacoustic and laser ultrasonic imaging. Specifically, robust methods inspired by compressive sampling theory are developed to compensate for the effects of the transducer impulse response and thermoelectrical noise in the measured data. Methods for estimating missing data also are developed, which require less data to be acquired and result in shortened the total imaging times. After the measured data have been pre-processed, a computationally efficient 3D FBP algorithm is employed for quantitative image reconstruction. The methods that are employed for achieving this are summarized below.

III. Sparsity-Regularized Data Restoration

An ultrasonic transducer's electromechanical impulse response (EIR) describes how its electro-acoustical properties degrade the recorded pressure data (47). In order to reconstruct an image that accurately depicts the absorbed optical energy density in OAT, the effect of the EIR on the measured optoacoustic signals must be accounted for. A robust method for measurement denoising and deconvolution of the EIR in OAT has been designed. This method deconvolves the EIR by solving the following constrained optimization problem:

$$\hat{\alpha} = \operatorname{argmin} \|\alpha\|_1 \text{ subject to } \|p - HC^{-1}\alpha\|_2 \leq \varepsilon \quad (1).$$

Here, $\alpha$ is the vector of expansion coefficients that correspond to the pressure data $p = C^{-1}\alpha$, $C^{-1}$ is the synthesis operator that relates the 3D pressure signal (two spatial coordinates plus time) to the expansion coefficients, and H is an operator that describes a 1D temporal blurring of the pressure data due to the EIR. The parameter E describes the noise level in the measured optoacoustic signals. The final estimate of the deconvolved pressure data is obtained as $\hat{p} = C^{-1}\hat{\alpha}$. The expansion functions used to represent the pressure data, which determines the explicit form for the operator $C^{-1}$, are chosen such that expansion coefficient vector $\alpha = Cp$ is sparse. Such expansion functions include curvelets. Although curvelet transform is known from the prior art (48), the method has not been developed before now for optoacoustic image reconstruction. Efficient and numerically robust algorithmic realizations of Eq. (1) are herein developed and optimized. Methods for estimating missing measurements of the pressure wavefield is developed by use of a generalization of Eq. (1) that has proven effective for a similar application in geophysical imaging (49).

This represents a fundamentally different approach for deconvolving the EIR in OAT. Specifically, the method is distinct from existing methods used in OAT in that it exploits sparsity of the pressure data in a suitably defined transform domain, and exploits the fact that the pressure signal produced by an optical absorber will yield a continuous wavefront in the measured data space. Similar methods have been employed for processing geophysical data (49) with great success. Results of this method using our new LOUIS imager are displayed in FIG. 19B. Use of the proposed method resulted in dramatically improved visibility of the blood-filled vessels and positive-valued pixel values that were proportional to the absorbed optical energy density within the tissue.

IV. 3D Iterative OAT Reconstruction Methods

The data restoration methods discussed supra facilitate accurate analytic image reconstruction. However, it is contemplated that iterative OAT reconstruction algorithms can improve diagnostic image quality for breast imaging applications. Iterative reconstruction algorithms offer the possibility to compensate for noise, instrument response, and other complicating factors related to the imaging physics. Iterative algorithms can mitigate data incompleteness, thereby permitting reduced data-acquisition times, but are more computationally burdensome than analytic methods, such as the FBP algorithm. An FBP algorithm is utilized to reconstruct an initial image for rapid viewing, while an iterative algorithm is utilized to reconstruct an improve image off-line for viewing at a later time (see FIGS. 20A-20B).

V. Limited Data Image Reconstruction

Iterative image reconstruction methods were developed based on constrained total-variation (TV) minimization (50). The idea of constrained TV-minimization has proven useful in the field of compressive sensing, and is effective when there exists some sparse representation of the object. Iterative reconstruction algorithms for tomography that operate via $L_1$-norm minzimization of the total variation (TV) of the object, subject to data consistency and object positivity constraints were examined. These results suggest that for certain classes of objects our reconstruction algorithms based on TV-minimization can significantly outperform conventional iterative algorithms, yielding informative images even when the measured data are highly incomplete. Other image reconstruction methods (51) inspired by compressive sampling are also adapted and explored for 3D OAT as described below. The developed algorithms compensate for the transducer EIR and also for the finite detection area of the transducer. The inventors have developed a methodology for modeling the response of an ultrasound transducer in iterative image reconstruction (29).

VI. Implementation on Graphics Processing Units (GPUs)

Because fully 3D iterative OAT image reconstruction can be computationally demanding, it is necessary to implement the developed algorithms using GPUs. Our team has specific expertise in the implementation of OAT image reconstruction algorithms using the NVidia CUDA programming environment. To demonstrate the speed-up factors that can be obtained, a preliminary study was conducted using an 8-core Intel Xeon processor workstation clocked at 2.40 GHz equipped with 48G memory and one NVIDIA Tesla C2050 GPU card with compute capability 2.0. An OAT experiment was simulated in which 360 transducers were evenly distributed on a measurement circle with 20 cm radius, and each transducer collected 256 samples at 2 MHz sampling rate. A 2D numerical phantom (256×256) was employed to represent the optical absorption distribution. Image reconstruction was performed by minimizing a least-squares cost function using a conjugate gradient method. The run time of the GPU code was 30 seconds while our CPU code took 1755 seconds to complete the reconstruction, resulting in a speed-up factor of approximately 60 for the GPU-based code. The cross-correlation of the two images was computed to be 0.9997, indicating that there was not a significant loss of accuracy by use of the GPU-based code. Our experience in this area permitted us to develop computationally feasible 3D reconstruction algorithms that facilitate their clinical applications.

VII. 3D UST and UST-Guided OAT Image Reconstruction Methods

3D UST image reconstruction methods are established for use with the developed multi-modal imager. Specialized UST-guided OAT reconstruction algorithms that compensate for variations in the SOS and attenuation properties of breast tissues were developed and implemented.

VIII. Reconstruction Methods for Sparse-Array 3D Ultrasound Tomography

Reconstruction methods are developed to form accurate images of the 3D acoustic properties of the breast. As described below, methods are developed for reconstructing images of three complementary breast properties: SOS, acoustic attenuation, and reflectivity. These 3D images provide a comprehensive description of breast anatomy that is complementary to the functional information revealed by the OAT image. These reconstruction methods account for problems that include mitigation of data incompleteness and noise and computationally tractably modeling of the relevant wave physics.

A. Reconstruction of SOS Distribution

Algorithms are developed for reconstructing the 3D SOS distribution the breast from knowledge of time-of-flight (TOF) measurements of the transmission ultrasound signals. Geometrical acoustic-based ray theory is utilized to establish a non-linear model that relates the measured TOF values to 3D SOS distribution as $$TOF(r_s, r_d) = \int_L \frac{1}{c(r)} dr, \quad (2)$$

where $TOF(r_s,r_d)$ is the TOF measured between source location $r_s$ and detector position $r_d$, $c(r)$ is the sought after SOS distribution, and $L=L(r_s,r_d;c(r))$ is the curved path traveled by the acoustic wave (that also depends on $c(r)$). For a given $c(r)$, the Eikonal equation (52) is solved numerically to determine the ray path L. An iterative reconstruction method is developed for inverting Eq. (2) that alternatively updates the estimates of $c(r)$ and L and minimizes a regularized cost function to obtain the final estimate of $c(r)$. It is contemplated that further development of algorithms can be guided by bent-ray ultrasound tomography that has shown promise in pre-clinical studies (16,17).

B. Reconstruction of Attenuation Distribution

Algorithms are developed for reconstructing the 3D acoustic attenuation distribution of the breast from transmission measurements. Accurate reconstruction of the acoustic attenuation requires knowledge of the SOS map and is therefore be conducted after the SOS map is determined using the methods described above. Given that the SOS map is known, a linear imaging model is obtained as $$a(r_s,r_d) = \int_L \alpha_0(r) dr \quad (3),$$

where $L=L(r_s,r_d;c(r))$ denote the same ray paths as determined from the last iteration of the alternating SOS reconstruction described above, and $\alpha_0(r)$ is a acoustic attenuation coefficient (31). The data function $a(r_s,r_d)$ is determined as an energy ratio between the measured transmission acoustic signal and the corresponding reference signal. Eq. (3) establishes a system of linear equations that is solved using established iterative methods from the medical image reconstruction literature. In particular, to mitigate artifacts due to noise and limited measurements, modern reconstruction methods, inspired by compressive sampling theory, is utilized for this task.

C. Reconstruction of Ultrasound Reflectivity

Algorithms developed for reconstructing the 3D distribution of acoustic reflectivity of the breast from knowledge of reflected, or backscattered, ultrasound data are provided. These algorithms are developed within the framework of 3D reflectivity tomography. In previous theoretical studies (24, 25), identified data redundancies were identified and it was demonstrated that accurate images could be reconstructed from backscattered acoustic echo data recorded on a sampled hemi-spherical measurement aperture. Based on that work, robust iterative reconstruction algorithms that incorporate the effects of the finite transducer size and finite sampling effects are developed.

IX. Ultrasound-Assisted OAT Image Reconstruction

In previous studies of OAT it was assumed that the object is acoustically homogeneous, which can limit image resolution. Reconstruction approaches for OAT that can compensate for acoustic heterogeneities in the determined SOS distribution via inversion of a generalized Radon transform (GRT) imaging model are developed. We have extensive experience with this topic (28). Perturbation theory for travel times is employed to incorporate higher-order diffraction effects into the GRT imaging model (28). This is based on a higher order geometrical acoustics generalization of the OAT imaging model that takes into account the first-order effect in the amplitude of the measured signal and second-order perturbation to the travel times that incorporate the effect of ray bending. Data redundancies are exploited to demonstrate that the GRT model can be inverted uniquely and stably by use of only half of the acquired measurement data. Iterative reconstruction approaches that permit explicit control of statistically complementary information that can result in the optimal reduction of image variances are developed. Methods based on time-reversal principles also are investigated. The effects of imperfect knowledge of the acoustic heterogeneity map also be investigated and robust methods developed to mitigate them. The development of such methods for compensating for acoustic attenuation is based on previous studies (26).

X. Optimization of Reconstruction Methods Via Computer-Simulation Studies

Computer-simulation studies are conducted to assess quantitatively the performance of the developed reconstruction algorithms. Realistic 3D numerical breast phantoms (16) are constructed that depict the acoustical and optical absorption properties of breast tissue. By use of these phantoms, simulation data is computed by solving the acoustic wave equation using the inventors' existing codes. Standard measures of physical image quality such as mean squared error is initially used to guide the development and optimization of the algorithms. The impact of physical factors such as stochastic noise, the finite bandwidth of the receiving ultrasound transducers, and the effects of finite sampling is investigated and compensated for. The developed algorithms are further refined and evaluated in the experimental studies described below that will quantify task-based image quality measures.

Evaluation Studies

I. Evaluation of the Imaging System Using Physical Phantoms

The imager and algorithm designs is informed and evaluated throughout the project by use of experimental studies that utilize well-characterized multi-modality phantoms made of either gelatin or poly(vinyl-chloride) plastisol (PVCP) and accurately mimicking optical and acoustic properties of the object or tissue of interest using $TiO_2$ as an optically scattering substance, various dyes for changing optical absorption and polystyrene and glass microspheres for changing acoustic properties of the phantoms.

Ultrasonic and optoacoustic phantoms exist or can readily be constructed. However, a single phantom that is appropriate for validating our dual-modality imaging system does not exist. Specialized dual-modality (US+OAT) phantoms that are well characterized can be constructed. These phantoms incorporate the optical scattering and absorption properties as well as the acoustic properties of breast tissue and are based on the inventors' hybrid phantoms for use with ultrasound tomography and diffuse optical tomography. Concentration of plastisol in PVCP was varied to achieve appropriate acoustic properties, for example, SOS, density, or attenuation. The use of glass microbeads to achieve tissue ultrasonic reflectivity were investigated.

For modeling the appropriate optical properties of breast tissue, i.e., index of refraction, absorption coefficient, scattering coefficient, and scattering anisotropy, dyes, India ink, and titanium oxide powder were used. PVCP has been shown to possess both optical and acoustic properties similar to tissue, Indian ink is a common optical absorbing material, $TiO_2$ powder is an established choice for modeling optical scattering, and small glass beads that are optically transparent is explored as a means of modeling acoustic attenuation of breast tissue. Blood-filled tumor-like inclusions are developed and use colored polymer threads are used for modeling microvessels. Ultrasonic and optoacoustic measurements are conducted to validate the phantoms.

II. Phantom Imaging Studies

Phantoms imaging studies are conducted to validate the imager and algorithms. Experimental parameters that are varied include the number of tomographic views acquired and the number of optoacoustic signals acquired at each transducer location that are averaged to improve SNR. The algorithms described herein are designed to reduce both of these quantities in order to minimize data-acquisition times. By use of phantoms that have tumors located at different depths and have different optical absorption properties, the sensitivity of the OAT system is quantified. Simplified versions of the phantoms are imaged for characterizing the spatially variant spatial resolution (42) and noise properties (60) of the reconstructed images. Additional image quality metrics employed in the imaging method are described below.

In-Vivo Imaging Studies

In Vivo Imaging System in Subjects with Tumors and Lesions Suspected as Malignant These in-vivo studies fine-tune the imaging system and image reconstruction algorithms and quantify breast cancer detection performance in a clinical setting. Breast cancer imaging represents the first in-vivo human application of multimode ultrasound/optoacoustic tomography, and yields preliminary data relevant to an evaluation of its clinical effectiveness. The system is highly effective for therapy monitoring, since laser optoacoustic functional and molecular imaging can reveal early physiological changes in blood supply, angiogenesis density and other molecular biomarkers.

The patient lies in the prone position on the examination table with the breast suspended through an opening into an imaging tank filled with sterile warm water based optoacoustic coupling medium. The imager surrounds the breast and collects the multi-wavelength OAT and ultrasound tomography measurement data. The multi-wavelength OAT measurements are acquired using laser wavelengths of 757 and 1064 nm, which permits differentiation of hypoxic and oxygenated blood. Data is acquired at 800 nm, where hypoxic and oxygenated blood absorb equally, i.e., the isosbestic point, which facilitates image normalization. The appropriate number of tomographic views to acquire to avoid conspicuous artifacts is based on the numerical and physical phantom studies. From these data, tomographic images representing the SOS, attenuation, reflectivity, and absorbed optical energy density are reconstructed onsite by use of the developed algorithms that are most computationally efficient. The measurement data is saved and is utilized for additional off-site processing by use of advanced image reconstruction algorithms and is utilized to refine the algorithms and systems provided herein.

Patient Population

The clinical study is performed according to an IRB protocol pending approval at MD Anderson Cancer Center. Patients with suspicious breast tumors identified by mammography and confirmed by ultrasound as BIRADS 4 and 5 and scheduled for biopsy undergo the multimode laser optoacoustic procedure prior to biopsy. As needed, breast MRI is performed on patients with ambiguous mammography and ultrasound images. Biopsy serves as the gold standard method to determine the tumor pathology. Patient information or other data with identifiers linked to the subjects is removed from any reports that can be taken outside the clinical Center.

Creation of Composite Multi-Parametric Images

The ultrasound tomography images, for example, SOS, attenuation, or reflectivity, may be fused into a single color-coded composite image. Human perception is not well suited to integrating diagnostic information presented in a set of related images viewed in parallel (61-63). It is contemplated that image fusion may facilitate the detection of breast cancer from the multi-parametric ultrasound images by a human observer (20). The imaging systems and methods provided herein are useful for forming a single composite image by use of linear (62) and non-linear (61) mappings of the single-parameter image values into red, green, and blue channels. These mappings can encode as much information as possible to help the expert reader. The evaluation methodology employed, including intra- and inter-observer analysis, is essentially similar to that employed by Alfano, et al. (64) for a multi-spectral MRI application. A similar methodology is utilized to summarize information regarding the functional OAT images in a single composite image. Thus, a composite OAT image depicting the total blood concentration can be color coded with a color of dominating level of oxygen saturation, so the radiologist can see the brightness based on the total blood content where the color tells him/her whether the blood is hypoxic or normally oxygenated.

As described below, the invention provides a number of advantages and uses, however such advantages and uses are not limited by such description. Embodiments of the present invention are better illustrated with reference to the Figure(s), however, such reference is not meant to limit the present invention in any fashion. The embodiments and variations described in detail herein are to be interpreted by the appended claims and equivalents thereof.

Figure 1A:
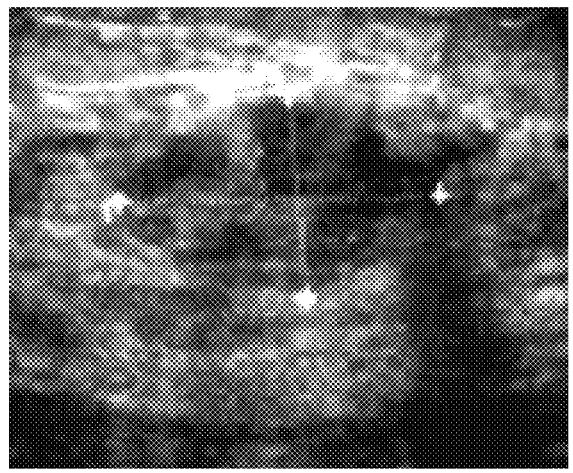
FIGS. 1A-1C depict two-dimensional images of a female's right cancerous breast in an an ultrasound image (FIG. 1A), an optoacoustic image (FIG. 1B) and an x-ray mammogram (FIG. 1C).
Figure 1B:
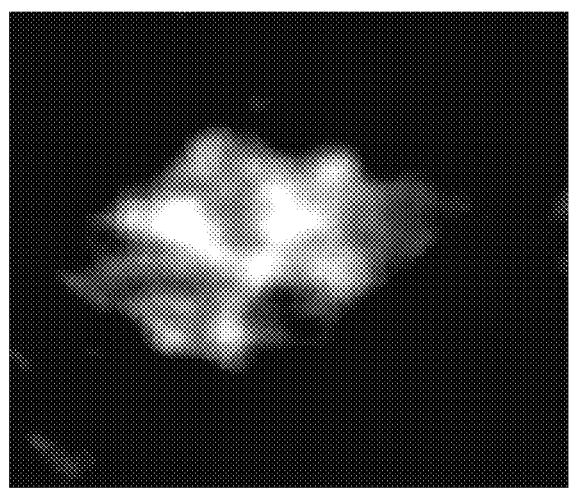
Figure 1C:
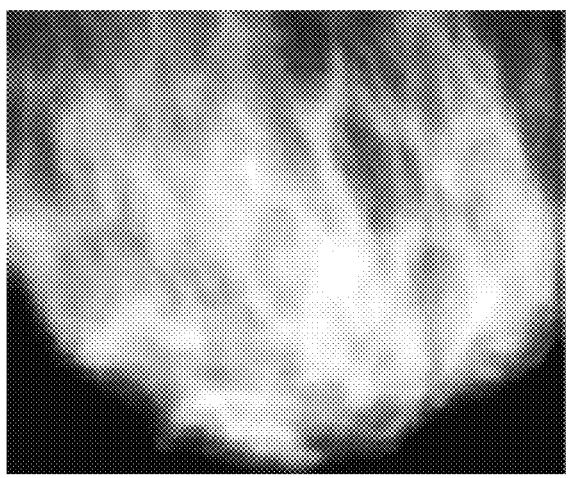

FIGS. 1A-1C illustrate the advantages of LOUIS in detection of breast cancer during examination and shows images of a portion of a human subject body with a cancerous tumor. In FIG. 1A an ultrasonic reflection image shows morphology of the subject body with volume of interest (tumor) based on a signal proportional to a product of density and speed of sound. In FIG. 1B an optoacoustic image shows the tumor based on signals proportional to concentration of the total hemoglobin in the tumor angiogenesis microvasculature. In FIG. 8C an X-ray mammography image of the same breast shows radiological density of the subject body with no contrast for the volume of interest that includes tumor. The X-ray image is inconclusive due to high breast density, but the presence of a tumor is confirmed by the ultrasound showing breast anatomy with enhanced tissue density in the tumor, and by the optoacoustic image showing high concentration of hypoxic blood in the tumor angiogenesis produced by the combined ultrasonic/optoacoustic system in diagnostic imaging of breast cancer.

Figure 2:
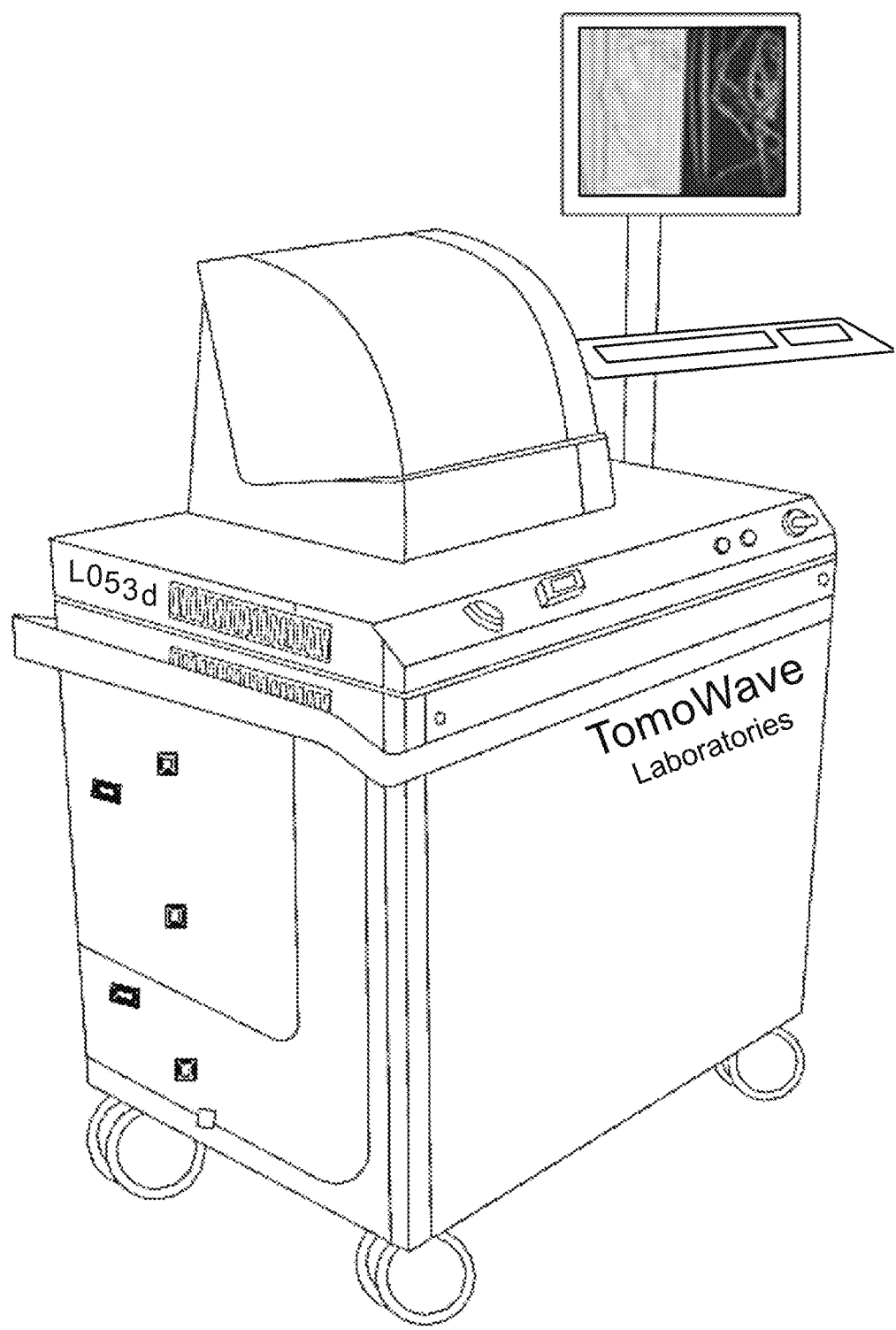
FIG. 2 shows the assembled laser optoacoustic ultrasonic system.

FIG. 2 is a photograph of the laser optoacoustic ultrasonic system as a fully assembled and operating prototype, demonstrating that this invention was reduced to practice. This tomography system has the following components and their technical specifications:

A. Pulsed Laser: Nd:YAG pumped Ti:Sapphire laser, Q-switched with pulse duration of 8 ns; wavelength tenability range ~532 nm, 730 nm to 850 nm, 1064 nm; pulse energy 120 mJ, pulse repetition rate 10 Hz, capability to toggle 2 wavelengths and tune continuously one wavelength.

B. Imaging module: Array of 128 ultrawide band ultrasonic transducers made of piezocomposite materials, 1×1 mm lateral dimensions, 5 MHz central frequency. Minimal detectable pressure by the system is about 1 Pa, which allows quantitative measurements of the optical absorption coefficient in the biomedical objects with accuracy of better than µa~0.01/cm. Three bifurcating fiber bundles with circular inputs and arc-shaped linear outputs that can be inserted in any of the 7 slots of the imaging module subject body. Plastic polymer caps cover outputs of the fiber bundles. The polymer caps are made transparent for optoacoustic imaging and black for laser ultrasonic imaging. Computer controlled rotational motor allows precise rotation and positioning of the imaging module around the biomedical object of interest. Typically, the module is rotated to 300 positions with 1.2 deg steps to acquire complete set of 3D data. This in turn generates 38400 virtual detectors on the spherical surface using 128 piezoelectric transducers, which results in accurate 3D images.

C. Electronics: The electronics are composed of 4×32 channel analog low noise high input impedance amplifier boards and 4×32 channel digital data acquisition boards with 12 bit ADCs and reconfigurable FPGA microprocessors for signal processing and transfer of the information to a computer for image reconstruction using multicore GPU Fermi video card. The system is computer controlled with dual core CPU.

Figure 3A:
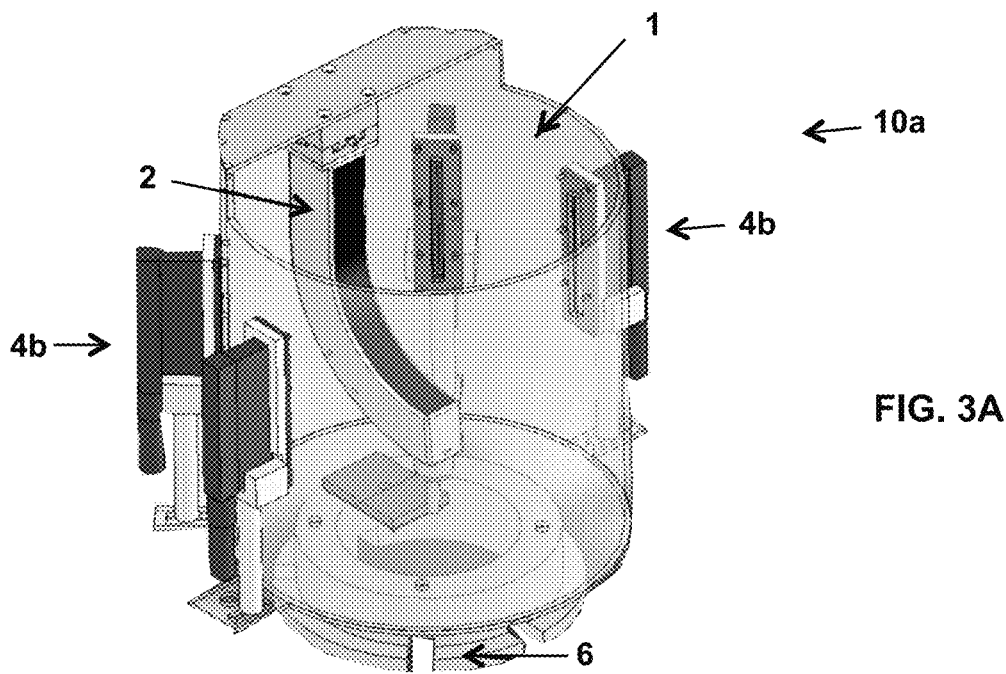
FIGS. 3A-3B depict the imaging module for the three-dimensional Laser Optoacoustic Ultrasound System (LOUIS-3D) with combined linear-flat plus arc shaped transducers (FIG. 3A) and with an arc-shaped transducer array (FIG. 3B).
Figure 3B:
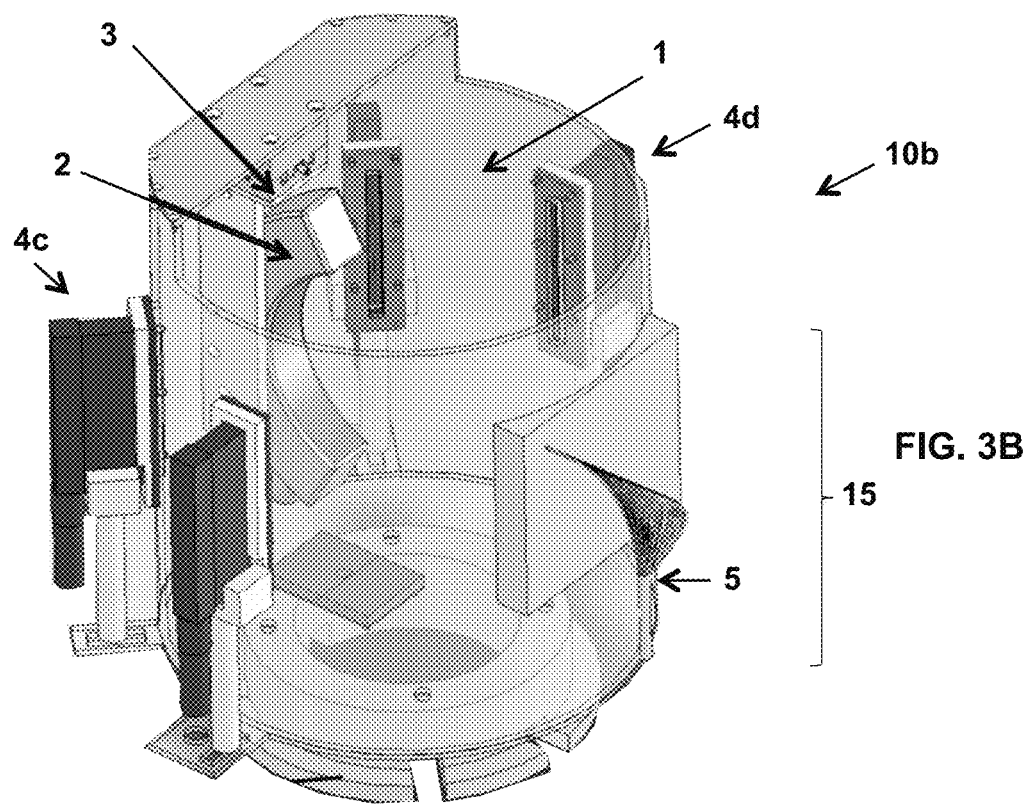
Figure 4A:
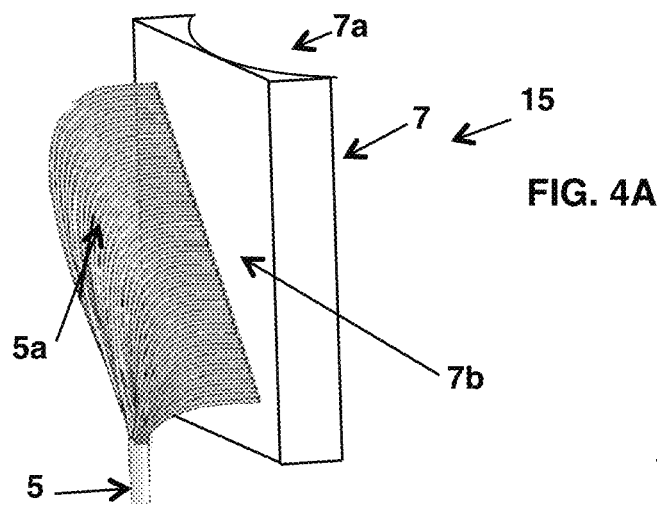
FIGS. 4A-4C are back, front and side views, respectively, of a laser ultrasonic emitter.
Figure 4B:
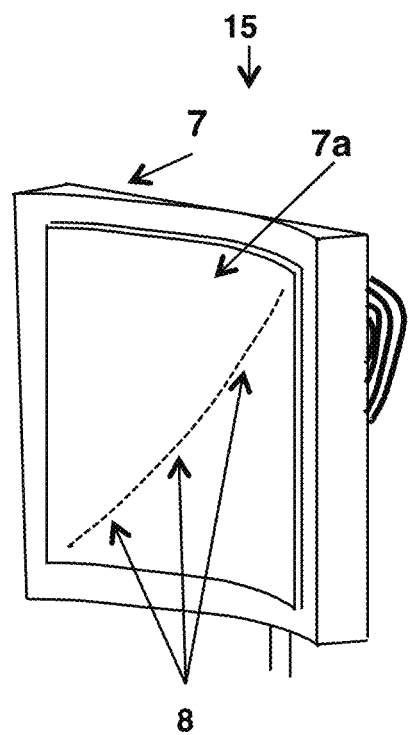
Figure 4C:
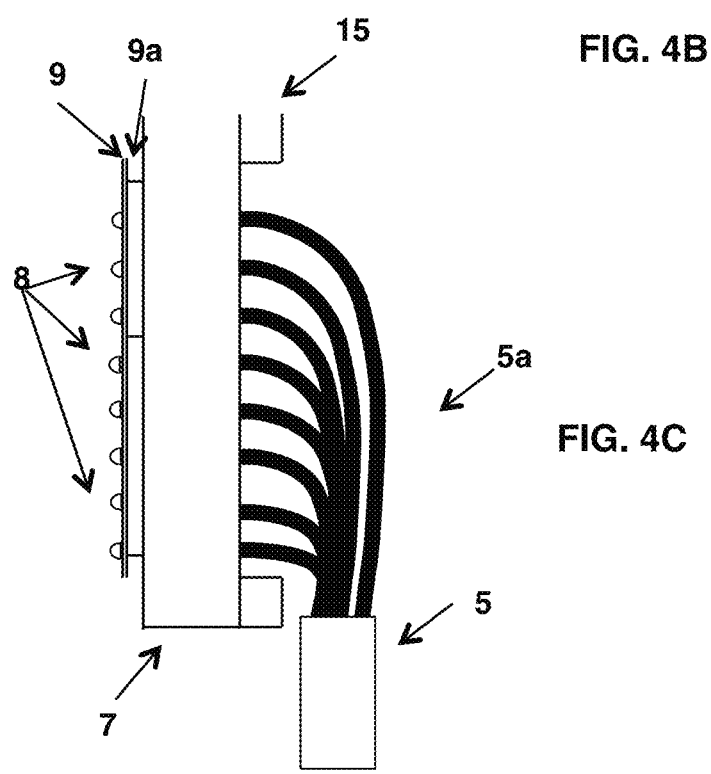

FIGS. 3A-3B are illustrations of the imaging modules for three-dimensional laser optoacoustic ultrasonic imaging system, LOUIS. FIG. 3A depicts a design suitable for optoacoustic imaging with combined linear-flat plus arc shaped combined array of ultrasonic transducers. FIG. 3B depicts a design suitable for laser ultrasonic plus laser optoacoustic imaging with arc-shaped array of ultrasonic transducers.

The imaging module 10 has a housing 1 made of hypoechoic acoustically absorbing and scattering material further electrically shielded with external metallization. An array of ultrawide-band ultrasonic transducers 2, optimized as detectors in the frequency range from 120 kHz to 12 Mhz, is a combined linear plus arc (J-shaped) array of 96 ultrawideband ultrasonic transducers and arc-shaped array of 128 ultrawide-band ultrasonic transducers. A translational X-Y-Z stage 3 provides flexibility for accurately placing the volume of interest close to the focal area of the ultrasound transducer array. A computer controlled rotational motor 6 allows precise rotational positioning of the imaging module relative to the volume of interest within a subject body.

Fiber bundles 4a,b,c,d for optoacoustic illumination optimally are made of 50 micron diameter glass fibers, about 12 mm diameter circular input and either flat rectangular outputs in 4a,b or arc-shaped linear outputs 4c,d. These 1-into-2 split bundles are designed with cylindrical lens to produce expanding beam of near-infrared laser illumination of tissue for optoacoustic imaging. Two pairs of bundles are placed in the imaging module. One pair 4a,c is placed closer to the detecting array of ultrasonic transducers for optoacoustic imaging of the skin outline in backward mode. The second pair 4b,d is placed facing each other, orthogonally to the detecting ultrasonic array and along the diameter of the imaging module for deep tissue optoacoustic imaging in orthogonal mode. Fiber bundle 5 for laser ultrasound generation optimally is made of 50 micron diameter glass fibers, about 12 mm diameter rectangular input for laser coupling and 33 outputs. I.e., a 1-into-33 split. each having circular output with a diameter of about 1 mm. This fiber bundle illuminates laser ultrasonic sources with short pulses of a laser operating at high pulse repetition rate of about 1280 to 2560 Hz.

With continued reference to FIGS. 3A-3B FIGS. 4A-4C are views of a laser ultrasonic emitter. The emitter 15 comprises fiberoptic illuminator holder 7, which is a plate that holds the outputs 5a of the fiber bundle 5 and is configured to functionally connect with the imaging module 10. The fiber bundle 5 comprises multiple sub-bundle outputs 5a, optimally about 32 to 64 sub-bundles. The sub-bundles are placed on a diagonal 7b to connect the top and bottom corners of the laser ultrasound emission aperture 7a. The laser ultrasound emission aperture optimally has a height greater than the height of the volume of interest in the subject body and the width corresponding to angular aperture greater than the width of the volume of interest. As an example an aperture of about 90 deg is shown. The range of angular apertures may vary with design from as small as 60 deg to as large as 150 deg depending on the dimensions of the volume of interest within the subject body.

A plurality of laser ultrasonic emitters, represented by 8, are hemispherical objects coated with thin layer of highly optically absorbing material for emission of laser ultrasound. Due to a finite diameter of the laser ultrasonic generator, the layer of the coating material should be spherically shaped to produce closer to ideal virtual spherical source of laser ultrasound. A plate-holder 9 holds the plurality of laser ultrasonic emitters 8, which are optimally separated at 9a from the outputs 5a of the glass optical fiber bundles 5 in order to provide non-reverberating Delta pulses of ultrasound in water-like optoacoustic coupling medium.

Figure 5A:
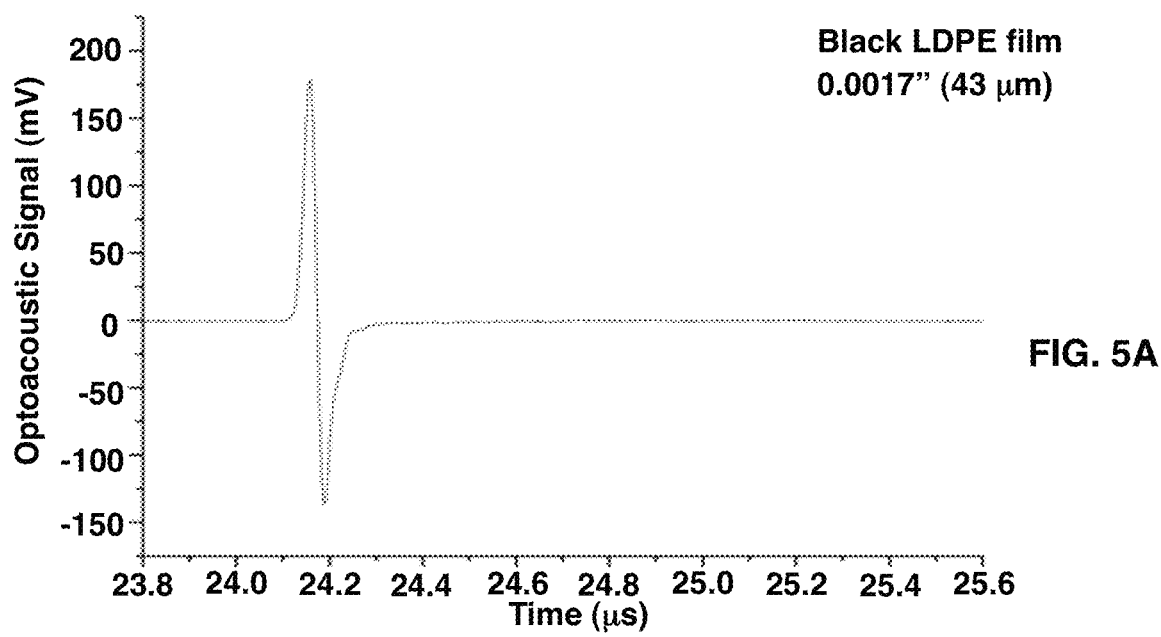
FIGS. 5A-5C depict the generation of Delta ultrasound pulses with high amplitude (FIG. 5A), ultrawide frequency spectrum (FIG. 5B) and wide directivity (FIG. 5C).
Figure 5B:
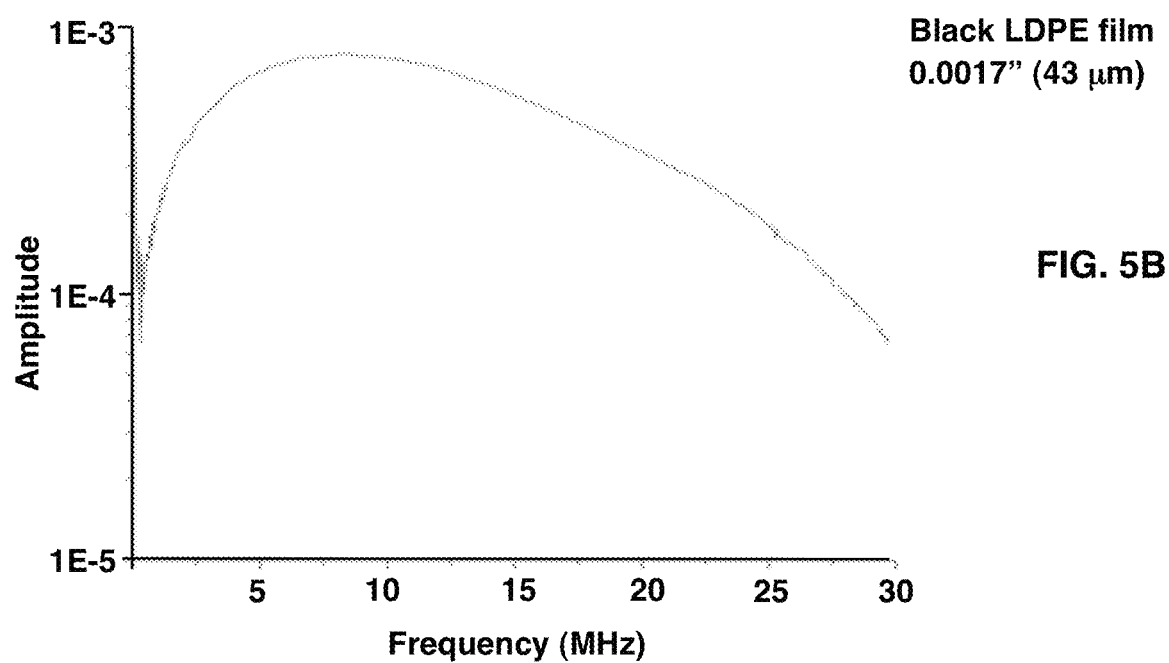
Figure 5C:
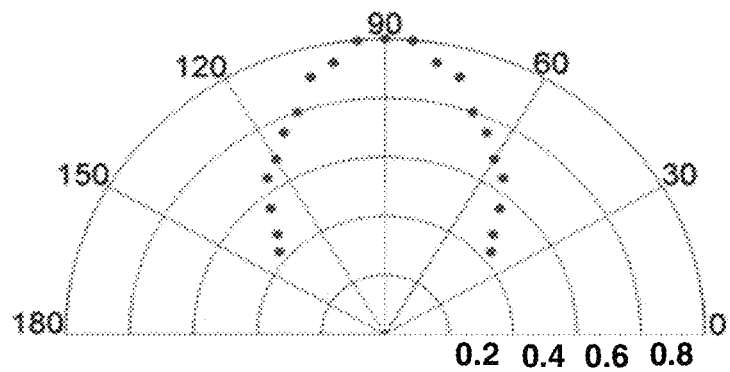

FIGS. 5A-5C illustrate advances in generation of short (so called, Delta) ultrasound pulses using lasers. FIGS. 5A-5C demonstrate that invented designs of laser ultrasound (LU) emitters produce short nonreverberating pulses of ultrasound with high amplitude (FIG. 5A) and ultrawide frequency spectrum (FIG. 5B). FIG. 5C shows wide directivity diagram of LU generation provided by a design with hemispherical tips of LU sources, which generated close to ideal ultrasonic waves with spherical wavefront. The design with spherical tips is preferred vs small flat sources due to wider directivity of the emitted LU. Based on this design other improved designs have been implemented. Efficiency of the designed LU source, LUE=5 [kPa]/[mJ/cm$^2$], and for the optimized spherical source coated with highly thermally expanding materials LUE can reach over 100 [kPa/[mJ/cm$^2$].

FIG. 6 is a table of Gruneisen parameters which is proportional to the efficiency of laser generation of ultrasound. Gruneisen parameter are presented for examples of liquid and solid materials with high thermal expansion and high speed of sound, which enables high laser ultrasound efficiency. The most important, however, is that the material will have very strong optical absorption at the laser wavelength employed for generation of ultrasound pulses. Such metals as gold and silver when made as thin layers possess plasmon resonance absorption which can be used for the benefit of LU generation. Alternatively, polymers such as PDMS or PMMA can be used for LU generation when colored with strongly absorbing molecules or particles.

Figure 7:
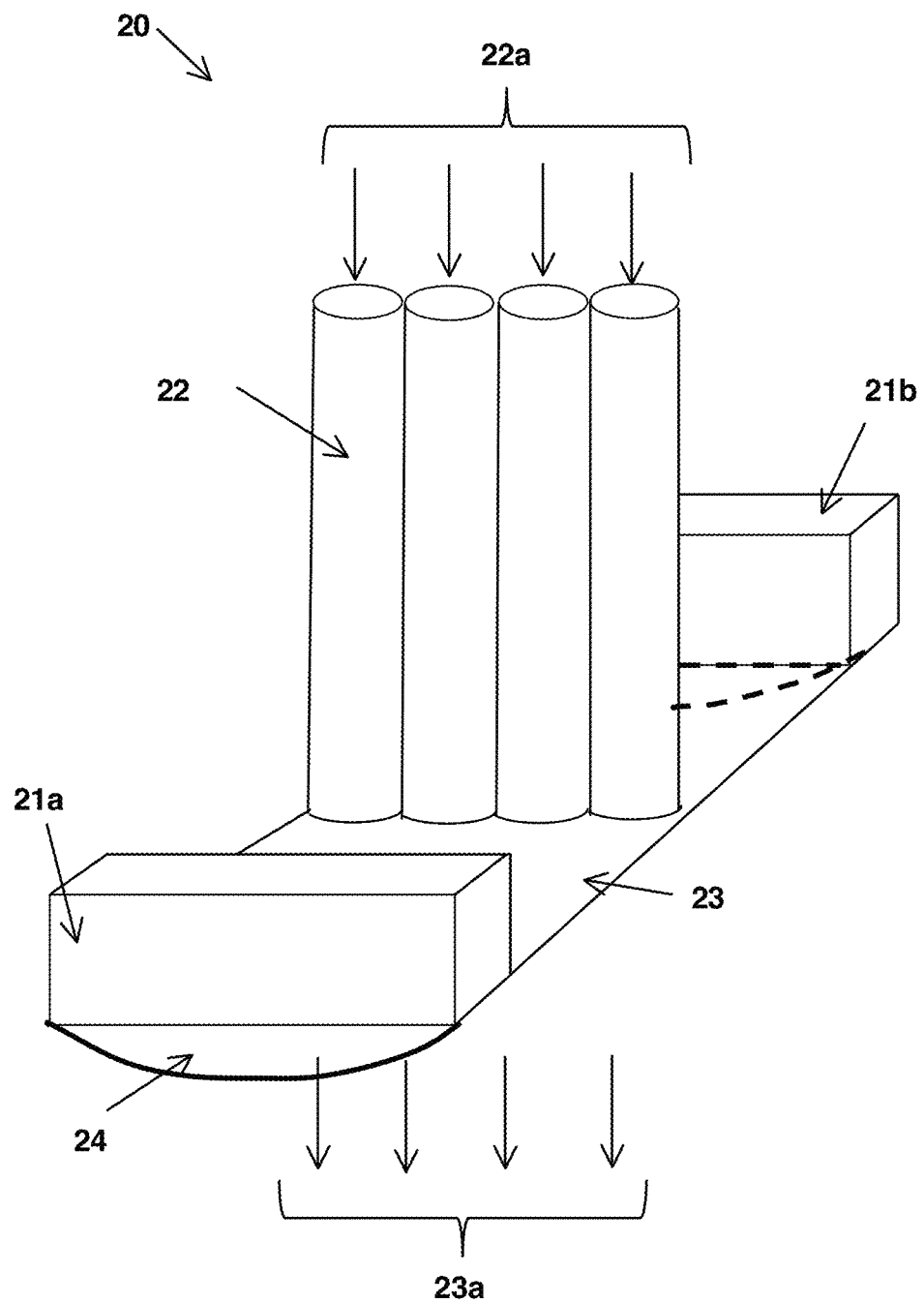
FIG. 7 depicts a hand-held probe comprising the imaging module.

FIG. 7 depicts a design of a hand-held probe for the 2D tomography system. Real-time laser ultrasonic imaging can be performed using a specially designed imaging module miniaturized as a hand-held probe 20. FIG. 7 shows two 4-6 mm ultrasonic transducers 21a,b as a portion of a linear array of 128 ultrasonic transducers. Fiberoptic bundle 22 is inserted between the two transducers to deliver laser pulses 22a to an optically absorbing layer 23, which generates ultrasound pulses 23a in response to the laser pulses. An acoustic lens 24 focuses the laser generated ultrasonic pulses into a thin slice of tissue in the volume of interest and also helps to collect reflected ultrasonic pulses also only from a thin layer of tissue being imaged. The acoustic lens can also serve as an ultrasound emitter, if made at least partially from materials that possess strong optical absorption and significant thermal expansion.

Figure 8A:
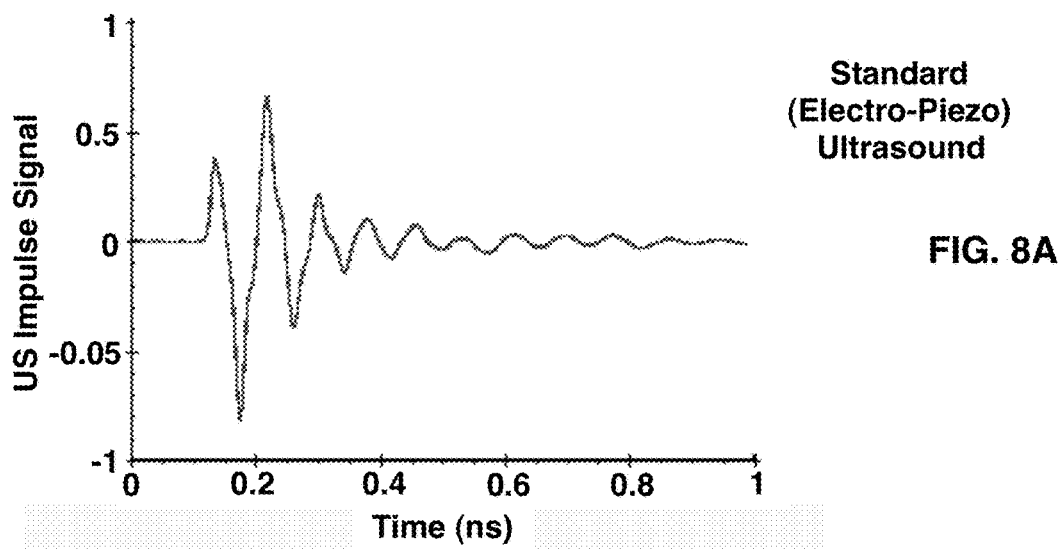
FIGS. 8A-8C are graphs of an electrically generated (FIG. 8A) and laser generated (FIG. 8B) ultrasound pulses and of the frequency spectrum (FIG. 8C) corresponding to FIG. 8B.
Figure 8B:
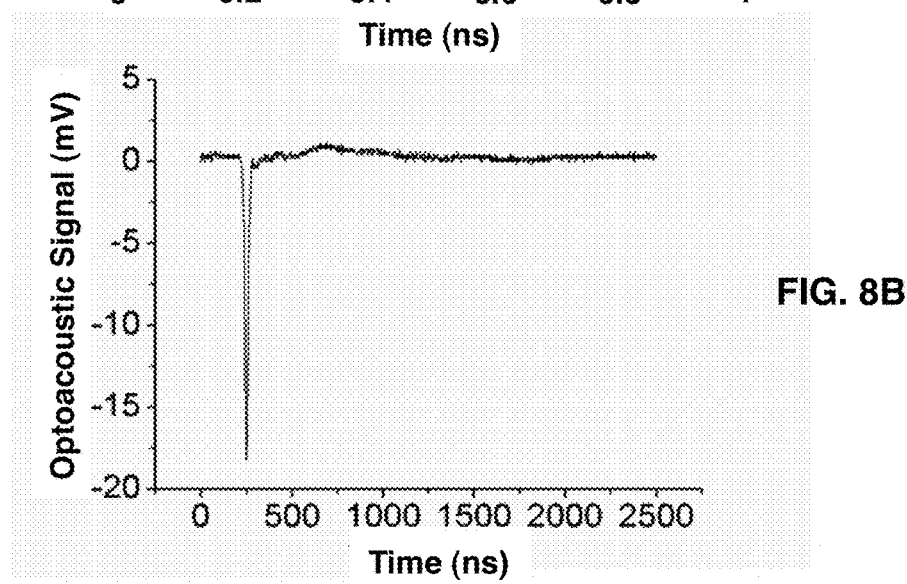
Figure 8C:
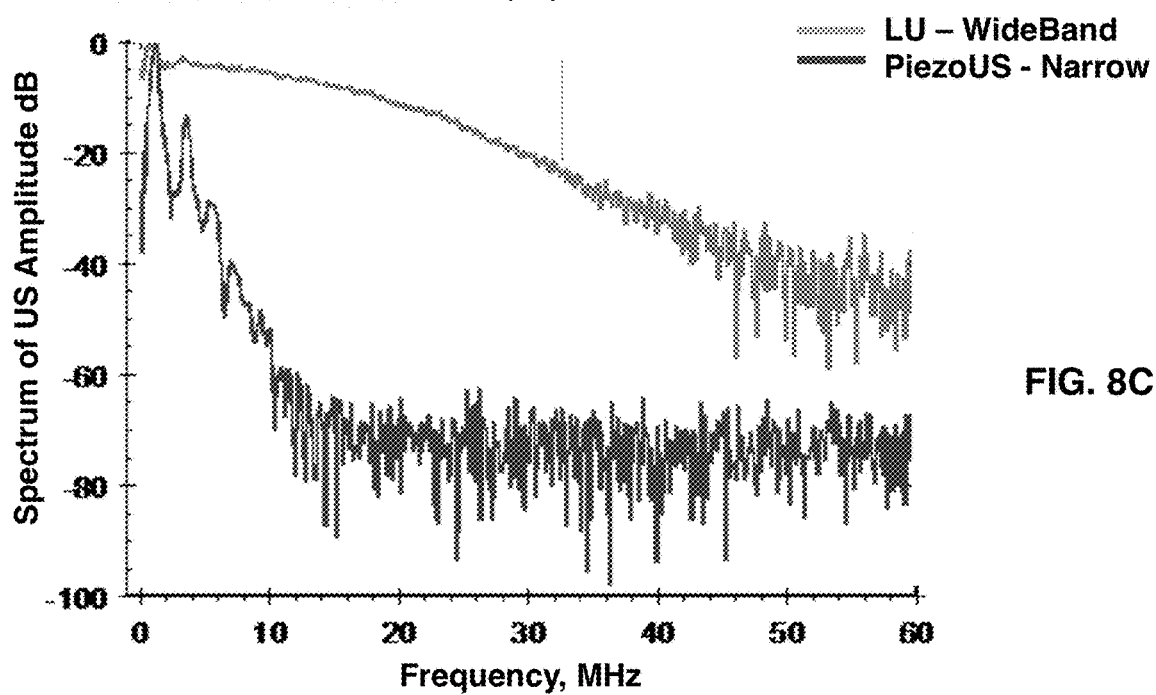

FIGS. 8A-8C demonstrate advantages of laser ultrasound pulses compared with electrically generated ultrasound pulses. Electrically generated ultrasound pulse (FIG. 8A) produced by a standard commercial ultrasonic transducer is strongly reverberating, so that an envelope of this pulse has to be used in reconstruction of images in ultrasound tomography. In contrast, laser generated pulse is non-reverberating and possess high amplitude. One skilled in the art can conclude from FIG. 8A and FIG. 8B, that laser ultrasound tomography can achieve spatial resolution about 3 times better than that of ultrasound that employs electrically generated ultrasonic pulses. FIG. 8C shows that ultrasonic frequency spectrum of laser ultrasound pulse is much wider compared with electrically generated ultrasound pulse. The ultrawide spectrum of ultrasonic frequencies available for laser ultrasound not only result in greater spatial resolution, but also can be used for ultrasonic spectroscopy as a method of tissues characterization with diagnostic purposes using ultrasonic imaging systems.

Figure 9A:
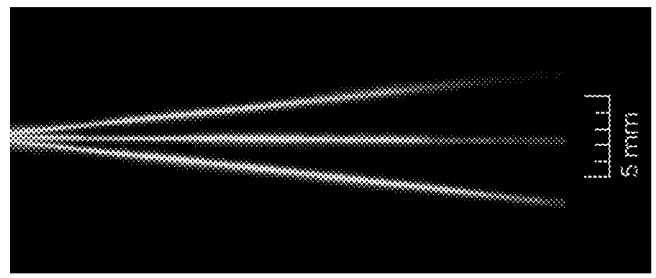
FIGS. 9A-9B depict three intersecting horse hairs (FIG. 9A) and the optoacoustic image brightness cross-section of one hair (FIG. 9B).
Figure 9B:
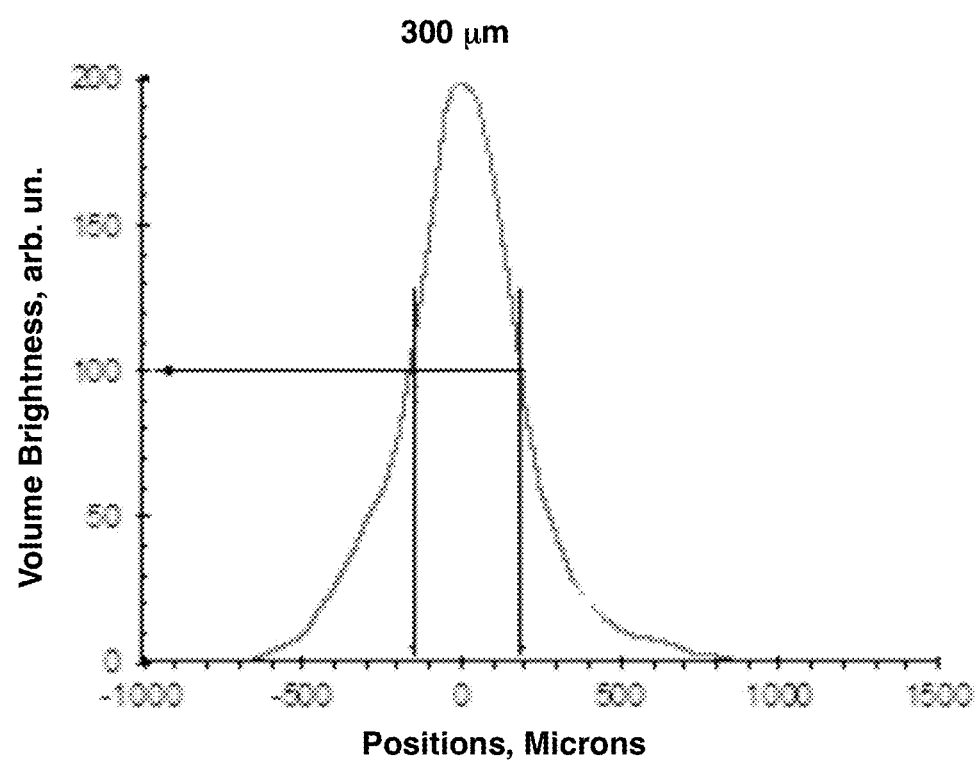

FIGS. 9A-9B are examples of spatial resolution achieved in LOUIS-3D system. In FIG. 9A three intersecting horse hairs were imaged as a subject body and the optoacoustic image brightness cross-section is presented for one of the hairs. The horse hairs had diameters about 100 to 150 micron. In FIG. 9B the image brightness shows Gaussian shape with FWHM equal to 300 micron. Such spatial resolution is achieved with detecting ultrasonic transducer array having sensitivity bandwidth from 150 kHz to 5 MHz. The image resolution can be further improved with widening the bandwidth of ultrasonic transducers, reduction of the transducer lateral dimensions and more accurate system alignment.

Figure 10A:
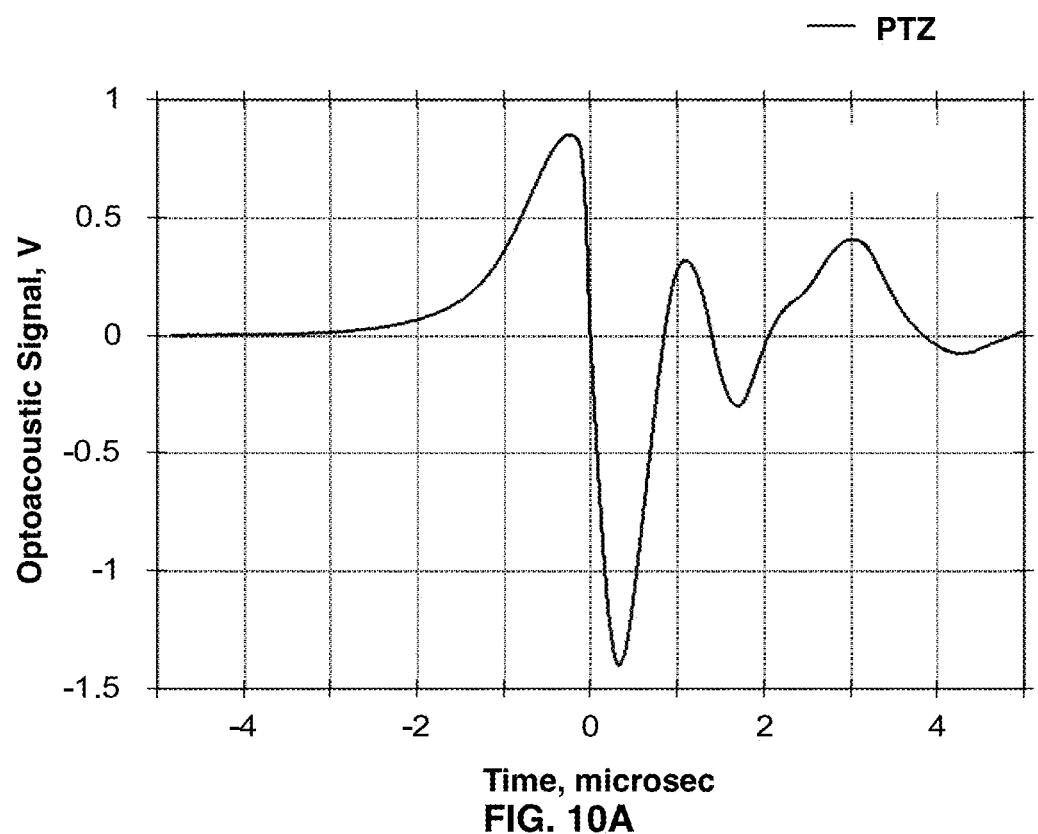
FIGS. 10A-10B depict optoacoustic profiles of a PZT (FIG. 10A) and of a single crystal PMN ceramic (FIG. 10B) ultrasonic transducers.
Figure 10B:
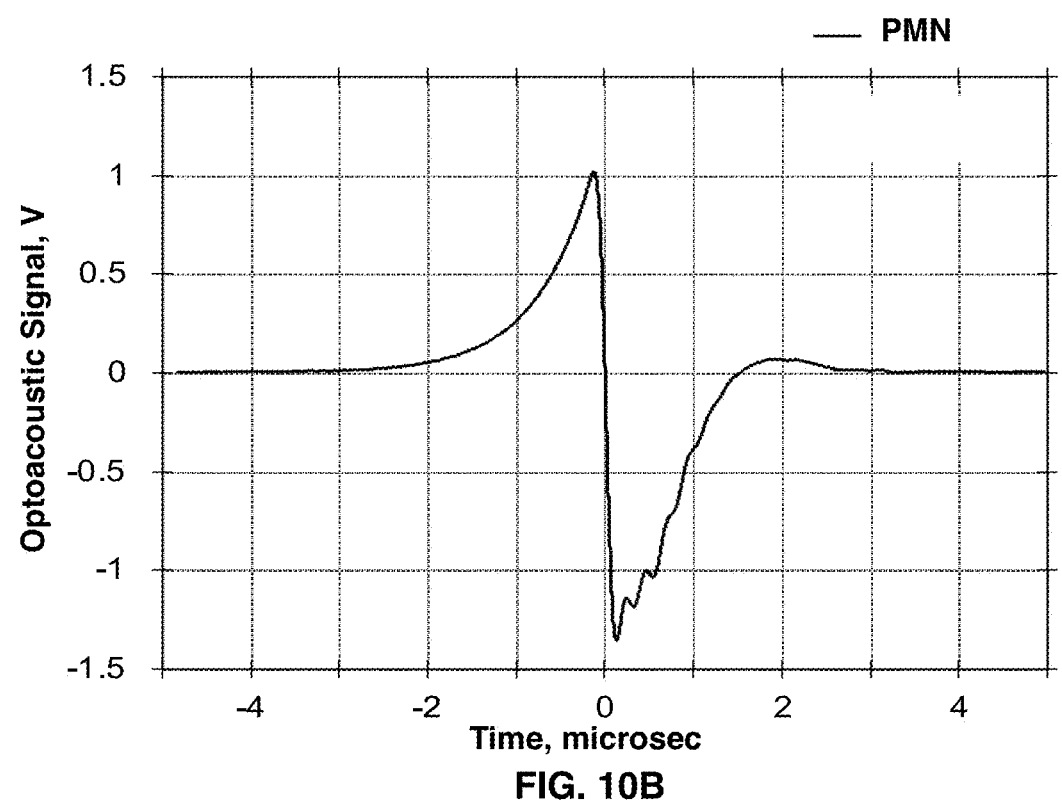

FIGS. 10A-10B illustrate the importance of ultrasonic transducers sensitive within ultrawide-band of ultrasonic frequencies. Optoacoustic profiles detected from an absorbing sphere by ultrasonic transducer made of PZT-standard relatively narrow band ultrasonic transducer (FIG. 10A) and a new ultrawide-band transducer made of single crystal PMN ceramic (FIG. 10B) are shown. A similar profile was observed from MPT single crystal ceramics. The profile in FIG. 10A is strongly reverberating, i.e. distorted, while the profile in FIG. 10B shows N-shaped non-reverberating pulse, which can be used for reconstruction of quantitatively accurate optoacoustic images of a sphere.

FIGS. 11A-11B are 2D projections of three-dimensional optoacoustic images of a skin outline of mouse subject body in vivo obtained with LOUIS-3D using illumination in backward mode. The laser illumination wavelength of 532 nm and the methods of signal and image processing were chosen to emphasize the skin surface. Knowledge of the skin outline permits separation of the volume inside the imaging module into two domains: the domain of the subject body and the external domain of the optoacoustic coupling medium. Since all properties of the coupling medium are well known, separation of the two domains allows much more accurate reconstruction of volumetric optoacoustic and ultrasonic images of the subject body.

Figure 12A:
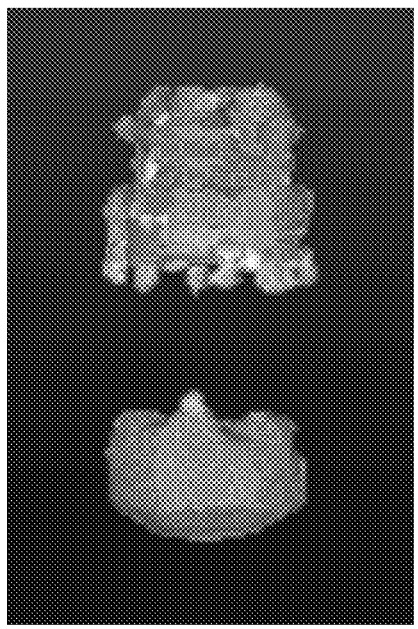
FIGS. 12A-12B illustrate the distribution of the speed of sound (FIG. 12A) and ultrasonic attenuation (FIG. 12B) in a phantom simulating a breast.
Figure 12B:

FIGS. 12A-12B illustrates that images of the speed of sound presents morphology with valuable diagnostic information. The image in FIG. 12A represents distribution of the speed of sound (SoS or SOS) in a phantom simulating a breast with tumors. Typically breast tumors have an SoS higher than that of normal breast tissues. The image of ultrasonic attenuation (UA) in FIG. 12B represents morphology with valuable diagnostic information, for example, the attenuation of fat and glandular tissues differ in the breast. In addition to diagnostic information, SoS and UA images allow correction of optoacoustic and ultrasonic images reconstruction algorithms in heterogeneous tissues. In a human subject body, anatomical ultrasonic imaging can provide morphology of background tissues, SoS and UA information and shape and structural features of tumors and blood vessels.

Figure 13:
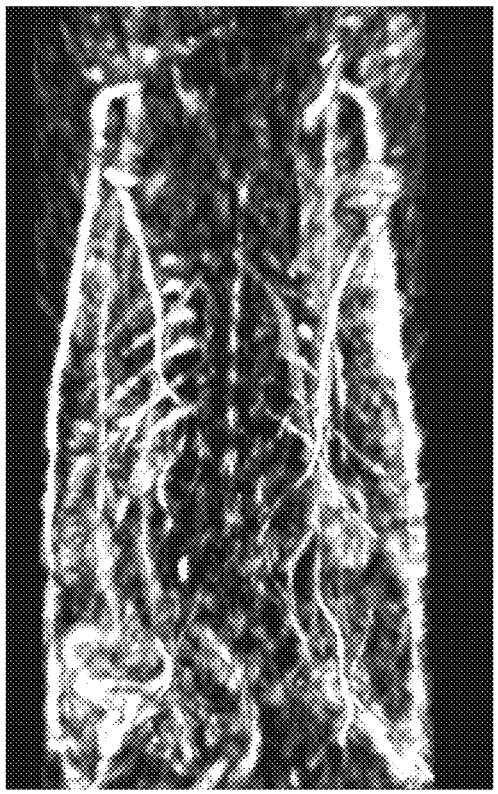
FIG. 13 is a 2D projection of an optoacoustic image of mouse body.

FIG. 13 shows a 2D projection of an optoacoustic image of mouse body. The image demonstrates that anatomical images can be produced by optoacoustic subsystem of LOUIS. Not only soft tissue organs and larger vasculature can be visualized, but also microvasculature of the skin, spine, ribs and joints.

FIG. 14 shows a 2D projection of a 3D LOUIS images of an animal subject body vasculature, i.e., angiography. Functional optoacoustic imaging can provide measurements of [Hb] and [HbO] (and total hematocrit) in tissues and blood vessels, assessment of heart function and blood flow, and assessment of tumor angiogenesis for diagnostic purposes. Microvessels as small as 50 micron are visible on LOUIS images due to high contrast (resolution 300 micron). Quantitative accuracy of the absorption coefficient was found about 0.1/cm in blood vessel phantoms.

FIG. 15 shows an exemplary optoacoustic image of brain vasculature of a live mouse. This type of imaging is important for detection and characterization of stroke and traumatic injury of the brain. This embodiment demonstrates capability of IOUIS for molecular imaging using exogenous contrast agents.

FIGS. 16A-16C shows 2D projections of 3D optoacoustic images of breast tumor receptors visualized using targeted contrast agent based on bioconjugated GNRs. Before injection of the contrast agent, mouse tumor (FIG. 16A) was visualized based on its microvasculature (FIG. 16B). After intravenous injection of gold nanorods (GNR) conjugated with PEG-Herceptin (FIG. 16C), distribution of targeted molecular receptors of HER2/neu in BT474 breast cancer cells became most contrasted feature. Quantitative information is the primary merit of optoacoustic imaging and can provide absolute values of the optical absorption coefficient and concentration of the most physiologically important molecules in the subject body.

FIGS. 17A-17B are exemplary 3D laser optoacoustic images of the breast acquired and reconstructed with LOUIS-3D. The laser wavelength used for illumination was 760 nm to emphasize veins and tissues with low blood-oxygen saturation level in the right breast (FIG. 17A) and 1064 nm to emphasize arteries and oxygenated tissue in the left breast (FIG. 17B). Optoacoustic orthogonal mode of illumination was used to acquire these images. Combination of Ultrasound and Optoacoustic Imaging also can be produced by LOUIS. One and the same probe and electronics hardware allows coregistration of ultrasonic and optoacoustic images, yielding complementary biomedical information.

FIG. 18 illustrates the method of optoacoustic image reconstruction with high accuracy of quantitative information based on data space restoration using curvelet transform followed by image reconstruction using filtered backprojection. This method is real time imaging method is equal or even more accurate than iterative methods of optoacoustic image reconstruction.

FIGS. 19A-19B show two optoacoustic images of a mouse vasculature reconstructed using standard filtered backprojection algorithm, which produces significant blurring and distortions (FIG. 19A) and filtered backprojection algorithm using optoacoustic signals processed with curvelet deconvolution method of data space restoration, which removes signal distortions associated with imperfection of the system hardware as well as alterations that occur in the course of propagation through tissues (FIG. 19B).

FIGS. 20A-20B show two images reconstructed using filtered back-projection algorithm taking entire set of measured optoacoustic signal data (FIG. 20A) and iterative algorithm taking only ¼ portion of the set of measured optoacoustic signal data (FIG. 20B). This example shows that the number of detecting transducers can be optimized by trading off small reduction in image quality for significant reduction in the data acquisition time and system cost. Based on the present design of LOUIS-3D and our understanding of iterative algorithms of 3D image reconstruction using sparse data, we teach here that LOUIS-3D is able to produce real-time volumetric images, i.e. acquire images with video rate of multiple frames per second. One possible design of the imaging module is a sphere sparsely but evenly covered with ultrasonic transducers, e.g. 512 detectors, which can acquire 3D images in one static position without any rotation around the object. With more and more powerful computers in future, it is contemplated that reconstruction of 3D images, i.e., large volumes with very high resolution. also can be accomplished faster than in 1 second.

The following references are cited herein.
1. Jemal et al. CA Cancer J. Clin. 2010; 60(4): 277-300.
2. P. C. Gotzsche and M. Nielsen: Cochrane Database Syst Rev. 2011; 1: CD001877. Review.
3. S. L. Edell and M. D. Eisen. Del Med J. 1999; 71(9): 377-382.
4. S W Fletcher and J G Elmore. Lancet 2005; 365(9453): 7-8.
5. Kumar et al. Molec. Med. 2005; 102(2): 138-141.
6. Conjusteau et al. Rev. Sci. Inst. 2009; 80: 093708 (1-5).
7. O'Donnell et al, Eur. Phys. J. Spec Topics—2008.
8. Oraevsky et al. Proc. SPIE 1994; 2134A: 122-128.
9. Oraevsky et al. U.S. Pat. No. 5,840,023 (31 Jan. 1996)
10. R. A. Kruger and P. Liu. Med. Phys. 1994; 21(7): 1179-1184.
11. R. A. Kruger U.S. Pat. No. 5,713,356 (4 Oct. 1996).
12. Brecht et al. J. Biomed. Optics 2009; 14(6), 0129061-8.
13. Pramanik et al. Medical Physics, 35, 2218-2223, 2008.
14. Ermilov et al. J Biomed Opt. 2009; 14(2): 024007 (1-14).
15. A. A. Oraevsky: Optoacoustic tomography of the breast, Chapter 33 in "Photoacoustic imaging and spectroscopy", ed. by L. Wang, Taylor and Francis Group, New York, 2009.
16. Manohar et al. Opt. Express 2007; 15(19), 12277-12285.
17. Kruger et al. Med. Phys, 2010; 37: 6096.
18. M. Xu and L.-H. Wang, Review of Scientific Instruments 77 (4), 041101, 2006.
19. Simonova et al. Moscow University Physics Bulletin, 2009; 64(4): 394-396.
20. Jose et al. Opt. Express 19, 2093-2104 (2011).
21. Duric et al. Med. Phys. 2007; 34, 773.
22. Glide-Hurst et al. Med. Phys. 37, 4526 (2010).
23. Li et al. Med. Phys. 37, 2233 (2010).
24. Glide-Hurst et al. Med. Phys. 35, 3988 (2008).
25. Li et al. Proc. SPIE, 6920, 692009 (2008)
26. Duric et al. Proc. SPIE 6920, 692000 (2008).
27. Zhang et al. IEEE Transactions on Medical Imaging, 28, pp. 1781-1790, 2009.
28. Modgil et al. J. Biomed. Opt., 15, 021308, 2010.
29. Wang et al. IEEE Transactions on Medical Imaging, 30, 203-214, 2011.
30. Shah et al. Proc Natl Acad Sci 2001; 98(8): 4420-4425.
31. Ghosh et al. Appl. Optics 2001; 40(1): 176-184.
32. Zhu et al. Radiology 2005; 237(1): 57-66. Erratum in: Radiology 2006; 239(2): 613.
33. Karabutov et al. Proc. SPIE 2000; 3916: 228-23934.
34. Oraevsky et al. Proc. SPIE 1999, 3597: 352-363.
35. Grosenick et al. Proc Natl Acad Sci 2001; 98(8): 4420-4425.
36. Ghosh et al. Appl. Optics 2001; 40(1): 176-184.
37. Andreev et al. IEEE Trans. UFFC 2003; 50(10): 1280-1287.
38. A. A. Karabutov and A. A. Oraevsky, Proc. SPIE 2000; 3916: 228-239.
39. Fessler and W. L. Rogers, "Resolution properties of regularized image reconstruction methods", Technical Report No. 297, Department of Electrical Engineering and Computer Science, The University of Michigan, 1996
40. Andreev et al. IEEE Trans. UFFC 2003; 50(10): 1280-1287.
41. A. A. Karabutov and A. A. Oraevsky. Proc. SPIE 2000; 3916: 228-239.
42. M. Xu and L. Wang. Phys. Rev. E, 71, 016706, 2005.
43. Oraevsky et al. "Optoacoustic Tomography", in Biomedical Photonics Handbook, ed. By T. Vo-Dinh, CRC Press, 2003, Vol. PM125, Chapter 34, pp. 34/1-34/34
44. Candes and D. Donoho. Wavelet Applications in Signal and Image Processing, 4119, 2000.
45. Chauris and T. Nguyen. Geophysics, 73, S35, 2008.
46. E. Y. Sidky and X. Pan, Phys. Med. Biol., 53, 4777-4807, 2008.
47. Guo et al. J. Biomed. Optics, 15, 021311, 2010.
48. Smith, M. Goldberg, and E. Liu, Ultrasonic Imaging, 2, 291-301, 1980.
49. Anderson, Journal of the Acoustical Society of America, 81, 1190-1192, 1987.
50. S. Kim, Geophysics, 67, 1225-1231, 2002.
51. S. Norton, "Journal of the Optical Society of America A, 4, 1919-1922, 1987.
52. Li et al. IEEE Int. Symp. Biomed. Imaging (ISBI), 896-899, (2006).
53. Anastasio et al. Proc. SPIE, 5750, 298-304 (2005).

This invention fulfills a longstanding need in the art for a tomography system that provides images based on ultrawide-band non-reverberating laser-induced ultrasonic pulsed signals. The system provides quantitative functional and molecular plus anatomical imaging through coregistered and mutually informed laser ultrasonic and optoacoustic images. The specifications and embodiments described herein serve to provide for disclosure of the following specific systems, methods and their biomedical applications.

What is claimed is:

1. A laser ultrasonic imaging system, consisting of:
a) a laser configured to deliver short pulses of optical energy of nanosecond duration to a plurality of laser ultrasonic emitters comprising optically absorbing particles embedded in polymers placed in specific locations configured for conversion of the absorbed optical energy into ultrasonic pulses within an ultrawide-band of ultrasonic frequencies from 50 KHz to 30 MHz;
b) the plurality of laser ultrasonic emitters comprising the optically absorbing particles embedded in polymers which are configured to generate ultrasonic pulses with known amplitude and ultrasonic frequency spectrum and configured to deliver said ultrasonic pulses at a given time through a coupling medium to a volume of interest in a subject;
c) a detector probe consisting of an array of ultrawide-band ultrasonic transducers that are sensitive to the range of the ultrasonic frequencies and configured to detect said ultrasonic pulses in multiple positions at or around said volume of interest and configured to convert said ultrasonic pulses into electronic signals, after said ultrasonic pulses are transmitted through or reflected from the volume of interest;
d) a data acquisition board consisting of an amplifier for analog amplification and analog-to-digital converter (ADC) for digital recording of said electronic signals;
e) a field programmable gate array (FPGA) microprocessor unit for performing signal processing;
f) a graphical processing unit (GPU) for image reconstruction; and
g) a central processing unit for system control, image processing and display.

2. The imaging system of claim 1, wherein said system is configured to produce in real time at a video rate images of two-dimensional slices based on measured parameters of the speed of sound, ultrasound attenuation or ultrasound backscattering.

3. The imaging system of claim 1, wherein said system is configured to produce three-dimensional images of the volume of interest in a subject body based on measured parameters of the speed of sound, ultrasound attenuation or ultrasound scattering.

4. The imaging system of claim 1, wherein the probe for detecting said ultrasonic pulses consists of a hand-held probe configured for acquisition, reconstruction and display of real-time two-dimensional or three-dimensional images.

* * * * *